United States Patent
Higuchi

(10) Patent No.: US 11,377,453 B2
(45) Date of Patent: *Jul. 5, 2022

(54) CRYSTAL OF COMPOUND HAVING JAK-INHIBITING ACTIVITY

(71) Applicant: NIPPON SHINYAKU CO., LTD., Kyoto (JP)

(72) Inventor: Fumi Higuchi, Kyoto (JP)

(73) Assignee: NIPPON SHINYAKU CO., LTD., Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/035,947

(22) Filed: Sep. 29, 2020

(65) Prior Publication Data

US 2021/0017191 A1  Jan. 21, 2021

Related U.S. Application Data

(63) Continuation of application No. 16/077,889, filed as application No. PCT/JP2017/007594 on Feb. 28, 2017, now Pat. No. 10,822,350.

(30) Foreign Application Priority Data

Mar. 1, 2016  (JP) .............................. JP2016-039315

(51) Int. Cl.
| | | |
|---|---|---|
| C07D 513/00 | (2006.01) | |
| A61P 29/00 | (2006.01) | |
| A61P 35/00 | (2006.01) | |
| A61P 37/06 | (2006.01) | |
| C07C 309/30 | (2006.01) | |
| A61K 31/506 | (2006.01) | |
| A61P 11/00 | (2006.01) | |
| A61P 25/00 | (2006.01) | |
| A61P 37/00 | (2006.01) | |
| C07D 513/04 | (2006.01) | |

(52) U.S. Cl.
CPC ............ *C07D 513/04* (2013.01); *A61P 29/00* (2018.01); *A61P 35/00* (2018.01); *A61P 37/06* (2018.01); *C07C 309/30* (2013.01); *C07B 2200/13* (2013.01)

(58) Field of Classification Search
CPC ........ C07D 513/04; A61P 29/00; A61P 35/00; A61P 37/06; A61P 11/00; A61P 25/00; A61P 37/00; C07B 2200/13; A61K 31/506
See application file for complete search history.

(56) References Cited

U.S. PATENT DOCUMENTS

| | | | |
|---|---|---|---|
| 4,918,073 A | 4/1990 | Ruger et al. | |
| 9,937,176 B2 | 4/2018 | Shiba et al. | |
| 10,822,350 B2 * | 11/2020 | Higuchi | ................. A61P 37/06 |
| 2011/0257165 A1 | 10/2011 | Pulici et al. | |
| 2017/0252341 A1 | 9/2017 | Shiba et al. | |

FOREIGN PATENT DOCUMENTS

| | | |
|---|---|---|
| JP | 2009-513571 A | 4/2009 |
| JP | 2011-136925 A | 7/2011 |
| JP | 2012-512837 A | 6/2012 |
| WO | 2005/066156 A1 | 7/2005 |
| WO | 2007/041130 A2 | 4/2007 |
| WO | 2007/084557 A2 | 7/2007 |
| WO | 2009/114512 A1 | 9/2009 |
| WO | 2010/010190 A1 | 1/2010 |
| WO | 2010/149769 A1 | 12/2010 |
| WO | 2011/075334 A1 | 6/2011 |
| WO | 2011/076419 A1 | 6/2011 |
| WO | 2011/086053 A1 | 7/2011 |
| WO | 2011/101161 A1 | 8/2011 |
| WO | 2012/022045 A1 | 2/2012 |
| WO | 2012/037132 A1 | 3/2012 |
| WO | 2012/054364 A2 | 4/2012 |
| WO | 2012/085176 A1 | 6/2012 |
| WO | 2013/025628 A1 | 2/2013 |
| WO | 2016/035814 A1 | 3/2016 |

OTHER PUBLICATIONS

T. Van Zele et al., "Differentiation of chronic sinus diseases by measurement of inflammatory mediators," Allergy, 61, pp. 1280-1289 (2006), The Authors Journal compilation/Blackwell Munksgaard.
Lucine Vuitton et al., "Janus Kinase Inhibition with Tofacitinib: Changing the Face of Inflammatory Bowel Disease Treatment," Current Drug Targets, vol. 14, No. 12, pp. 1385-1391 (2013), Ingenta.
D. J. Wallace et al., "MEDI-545, an Anti-Interferon Alpha Monoclonal Antibody, Shows Evidence of Clinical Activity in Systemic Lupus Erythematosus," presented at ACR Concurrent Session SLE: Novel Therapies (Nov. 9, 2007), pp. S526-S527.
Shumpei Yokota et al., "Efficacy and safety of tocilizumab in patients with systemic-onset juvenile idiopathic arthritis: a randomised, double-blind, placebo-controlled, withdrawal phase III trial," The Lancet, vol. 371, pp. 998-1006, (Mar. 22, 2008), Elsevier Ltd.
Xiaoting Zhang et al., "Lesional infiltration of mast cells, Langerhans cells, T cells and local cytokine profiles in alopecia areata," Archives of Dermatological Research, vol. 307, pp. 319-331 (2015), Springer Nature.
Norihiro Nishimoto et al., "Toxicity, Pharmacokinetics, and Dose-Finding Study of Repetitive Treatment with the Humanized Anti-Interleukin 6 Receptor Antibody MRA in Rheumatoid Arthritis. Phase I/II Clinical Study," The Journal of Rheumatology, vol. 30, Issue 7, pp. 1426-1435 (2003).

(Continued)

*Primary Examiner* — John M Mauro

(57) ABSTRACT

An object of the present invention is to provide a compound with an excellent JAK1 inhibitory activity.
The compound of the invention has JAK1 inhibitory activity, and thus, immunosuppressive effect, anti-inflammatory effect, anti-proliferative effect and so on, and is useful in the treatment of the diseases, for example, rheumatoid arthritis, inflammatory bowel disease, psoriasis, vasculitis, bronchial asthma, chronic obstructive pulmonary disease, eosinophilic sinusitis and nasal polyp.

12 Claims, 2 Drawing Sheets

(56) References Cited

OTHER PUBLICATIONS

International Searching Authority, "Written Opinion," issued in International Application No. PCT/JP2017/007594, of which U.S. Appl. No. 16/077,889 is a U.S national phase entry, with a date of mailing of May 9, 2017, 6 pages.

Norihisa Ogata et al., "JAK2 and JAK1 Constitutively Associate With an Interleukin-5 (IL-5) Receptor α and βc Subunit, Respectively, and Are Activated Upon IL-5 Stimulation," Blood, vol. 91, No. 7 (Apr. 1, 1998), pp. 2264-2271, American Society of Hematology.

Murray Zanger PhD et al., "Structure-Activity Relationship and Drug Design," Remington's Pharmaceutical Sciences, Sixteenth Edition, pp. 420-425 (1980), Mack Publishing Company.

Stephen M. Berge et al., "Pharmaceutical Salts," Journal of Pharmaceutical Sciences, vol. 66, No. 1, pp. 1-19 (Jan. 1977), Elsevier Inc.

Andrea Gioffredi et al., "Eosinophilic granulomatosis with polyangiitis: an overview," Frontiers in Immunology, vol. 5, Article 549, pp. 1-7 (Nov. 2014).

Alfred Mahr et al., "Eosinophilic granulomatosis with polyangiitis (Churg-Strauss): evolutions in classification, etiopathogenesis, assessment and management," Current Opinion in Rheumatology, vol. 26, No. 1, pp. 16-23, (Jan. 2014), Wolters Kluwer Health, Inc.

United States Patent and Trademark Office, "Restriction Requirement," issued in U.S. Appl. No. 16/077,889, with a notification date of Dec. 27, 2018, 8 pages.

United States Patent and Trademark Office, "Non-Final Office Action," issued in U.S. Appl. No. 16/077,889, with a notification date of Mar. 29, 2019, 8 pages.

United States Patent and Trademark Office, "Final Office Action," issued in U.S. Appl. No. 16/077,889, with a notification date of Jul. 30, 2019, 9 pages.

United States Patent and Trademark Office, "Advisory Action," issued in U.S. Appl. No. 16/077,889, with a notification date of Nov. 21, 2019, 4 pages.

Jun Abe, "Cytokines in Kawasaki disease,"Nippon Rinsho, vol. 72, No. 9, pp. 1548-1553 (Sep. 2014).

N. Akdeniz et al., "Serum Interleukin-2, Interleukin-6, Tumour Necrosis Factor-Alpha and Nitric Oxide Levels in Patients with Behcet's Disease," ANNALS Academy of Medicine Singapore, vol. 33, No. 5, pp. 596-599 (Sep. 2004).

Sabina A. Antoniu, "Pitrakinra, a dual IL-4/IL-13 antagonist for the potential treatment of asthma and eczema," Current Opinion in Investigational Drugs, vol. 11, No. 11, pp. 1286-1294 (2010).

Manabu Araki et al., "Efficacy of the anti-IL-6 receptor antibody tocilizumab in neuromyelitis optica—A pilot study," Neurology, vol. 82, pp. 1302-1306 (Apr. 15, 2014), American Academy of Neurology.

Lei Bao et al.," I he involvement of the JAK-STAT signaling pathway in chronic inflammatory skin disease atopic dermatitis," JAK-STAT, vol. 2, Issue 3, pp. e24137-1-e24137-8 (Jul./Aug./Sep. 2013).

Michiel Beekhuizen et al., "Inhibition of Oncostatin M in Osteoarthritic Synovial Fluid Enhances GAG Production in Osteoarthritic Cartilage Repair," European Cells & Materials Journal, vol. 26, pp. 80-90 (2013).

Paula Brown et al., "Single nucleotide polymorphisms (SNPs) in key cytokines may modulate food allergy phenotypes," European Food Research and Technology, doi: 10.1007/s00217-012-1827-3 (Published online: Sep. 23, 2012), Springer-Verlag.

Paul J. Christner and Sergio A. Jimenez, "Animal models of systemic sclerosis: insights into systemic sclerosis pathogenesis and potential therapeutic approaches," Current Opinion in Rheumatology, vol. 16, pp. 746-752 (2004).

Ana P Costa-Pereira et al., "Dysregulation of janus kinases and signal transducers and activators of transcription in cancer," American Journal of Cancer Research, 1 (6), pp. 806-816 (2011).

Marinos C. Dalakas, "Biologies and other novel approaches as new therapeutic options in myasthenia gravis: a view to the future," Annals of the New York Academy of Sciences, 1274, pp. 1-8 (2012), New York Academy of Sciences.

Javier Donate-Correa et al., "Inflammatory Cytokines in Diabetic Nephropathy," Journal of Diabetes Research, vol. 2015, Article ID 948417, 9 pages (2015), Hindawi Publishing Corporation.

J. Dong et al., "Activation of the STAT1 signalling pathway in lupus nephritis in MRL/Ipr mice," Lupus, 16, pp. 101-109 (2007), SAGE Publications.

Emily Yiping Gan et al., "Therapeutic Strategies in Psoriasis Patients with Psoriatic Arthritis: Focus on New Agents," BioDrugs, 27, pp. 359-373 (2013), Adis International.

Maria Gliozzi et al., "A link between interferon and augmented plasmin generation in exocrine gland damage in Sjögren's syndrome," Journal of Autoimmunity, 40, pp. 122-133 (2013), Elsevier Ltd.

Takahisa Gono et al., "Cytokine profiles in polymyositis and dermatomyositis complicated by rapidly progressive or chronic interstitial lung disease," Rheumatology, 53, pp. 2196-2203 (2014).

Takashi Goto et al., "Increase in B-cell-activation factor (BAFF) and IFN-γ productions by tonsillar mononuclear cells stimulated with deoxycytidyl-deoxyguanosine oligodeoxynucleotides (CpG-ODN) in patients with IgA nephropathy," Clinical Immunology, vol. 126, pp. 260-269 (2008), Elsevier Inc.

Bora Gülhan et al., "Studying cytokines of T helper cells in the kidney disease of IgA vasculitis (Henoch-Schönlein purpura)," Pediatric Nephrology, vol. 30, pp. 1269-1277 (2015), Springer Nature.

Claude Haan et al., "Jak1 Has a Dominant Role over Jak3 in Signal Transduction through γc-Containing Cytokine Receptors," Chemistry & Biology, vol. 18, pp. 314-323 (Mar. 25, 2011), Elsevier Ltd.

Tamihiro Kawakami et al., "Serum Levels of Interleukin-6 in Patients with Cutaneous Polyarteritis Nodosa," Acta Dermato-Venereologica, Vo. 92, pp. 322-323 (2012).

P. Kieffer et al., "Efficacité clinique et biologique du tocilizumab au cours de la maladie de Horton: à propos de trois observations et revue de la littérature," La Revue de Médecine Interne, vol. 35, pp. 56-59 (2014), Elsevier Masson SAS.

Hirohito Kita et al., "Cytokine Production at the Site of Disease in Chronic Eosinophilic Pneumonitis," American Journal of Respiratory and Critical Care Medicine, vol. 153, pp. 1437-1441 (1996), American Thoracic Society.

A.C. Muller Kobold et al., "In vitro up-regulation of E-selectin and induction of interleukin-6 in endothelial cells by autoantibodies in Wegener's granulomatosis and microscopic polyangiitis," Clinical and Experimental Rheumatology, vol. 17, pp. 433-440 (1999).

Taku Kouro and Kiyoshi Takatsu, "IL-5- and eosinophil-mediated inflammation: from discovery to therapy," International Immunology, vol. 21, No. 12, pp. 1303-1309 (2009), Japanese Society for Immunology.

Janusz J. Kulagowski et al., "Identification of Imidazo-Pyrrolopyridines as Novel and Potent JAK1 Inhibitors," Journal of Medicinal Chemistry, vol. 55, pp. 5901-5921 (2012), ACS Publications.

Fanny Legrand and Amy D. Klion, "Biologic Therapies Targeting Eosinophils: Current Status and Future Prospects," Journal of Allergy and Clinical Immunology in Practice, vol. 3, Issue 2, pp. 167-174 (Mar./Apr. 2015), Elsevier Inc.

Jun Li et al., "INCB16562, a JAK1/2 Selective Inhibitor, Is Efficacious against Multiple Myeloma Cells and Reverses he Protective Effects of Cytokine and Stromal Cell Support," Neoplasia, vol. 12, No. 1. pp. 28-38 (Jan. 2010), Elsevier Inc.

Sung A. Lim et al., "Association of IL-21 Cytokine With Severity of Primary Sjogren Syndrome Dry Eye," Cornea, vol. 34, No. 3, pp. 248-252 (Mar. 2015), Wolters Kluwer Health, Inc.

Jeremiah P. Malerich et al., "Diamino-1,2,4-triazole derivatives are selective inhibitors of TYK2 and JAK1 over JAK2 and JAK3," Bioorganic & Medicinal Chemistry Letters, vol. 20, pp. 7454-7457 (2010), Elsevier Ltd.

(56) References Cited

OTHER PUBLICATIONS

Masatsugu Masuda et al., "Correlations of Inflammatory Biomarkers With the Onset and Prognosis of Idiopathic Sudden Sensorineural Hearing Loss," Otology & Neurotology, vol. 33, No. 7, pp. 1142-1150 (2012).

Javier Mendiola et al., "Preparation, Use, and Safety of O-Mesitylenesulfonylhydroxylamine," Organic Process Research & Development, vol. 13, pp. 263-267 (2009), ACS Publications.

Masahiko Mihara et al., "IL-6/IL-6 receptor system and its role in physiological and pathological conditions," Clinical Science, vol. 122, pp. 143-159 (2012), The Authors Journal compilation/Biochemical Society.

M. Nabavi et al., "Increased level of interleukin-13, but not interleukin-4 and interferon-γ in chronic rhinosinusitis with nasal polyps," Allergologia et Immunopathologia, 42(5), pp. 465-471 (2014), Elsevier España S.L.U.

Takashi Nanba et al., "Increases of the Th1/Th2 Cell Ratio in Severe Hashimoto's Disease and in the Proportion of Th17 Cells in Intractable Graves' Disease," Thyroid, vol. 19, No. 5, pp. 495-501 (2009), Mary Ann Liebert, Inc.

Björn Nashan et al., "Randomised trial of basiliximab versus placebo for control of acute cellular rejection in renal allograft recipients," The Lancet, vol. 350, pp. 1193-1198 (Oct. 25, 1997), Elsevier Ltd.

Markus F. Neurath and Susetta Finotto, "IL-6 signaling in autoimmunity, chronic inflammation and inflammation-associated cancer," Cytokine & Growth Factor Reviews, vol. 22, pp. 83-89 (2011), Elsevier Ltd.

Norihiro Nishimoto et al., "Improvement in Castleman's disease by humanized anti-interleukin-6 receptor antibody therapy," Blood, vol. 95, No. 1, pp. 56-61 (Jan. 2000), American Society of Hematology.

John J. O'Shea and Robert Plenge, "JAKs and STATs in Immunoregulation and Immune-Mediated Disease," Immunity, vol. 36, Issue 4, pp. 542-550 (Apr. 20, 2012), Elsevier Inc.

Lynda A. O'Sullivan et al., "Cytokine receptor signaling through the Jak-Stat-Socs pathway in disease," Molecular Immunology, vol. 44, pp. 2497-2506 (2007), Elsevier Ltd.

Alfonso Quintás-Cardama et al., "Janus kinase inhibitors for the treatment of myeloproliferative neoplasias and beyond," Nature Reviews Drug Discovery, vol. 10, pp. 127-140 (Feb. 2011), Springer Nature.

D. Saadoun et al., "Th1 and Th17 Cytokines Drive Inflammation in Takayasu Arteritis," Arthritis & Rheumatology, vol. 67, No. 5, pp. 1353-1360 (May 2015), American College of Rheumatology.

Osamu Sakai et al., "Involvement of NFκB in the Production of Chemokines by Rat and Human Conjunctival Cells Cultured Under Allergenic Conditions," Current Eye Research, vol. 38, Issue 8, pp. 825-834 (2013), Informa Healthcare USA, Inc.

Anette G. Sams et al., "Discovery of N-{1-[3-(3-Oxo-2,3-dihydrobenzo[1,4]oxazin-4-yl)propyl]piperidin-4-yl}-2-phenylacetamide (Lu AE51090): An Allosteric Muscarinic M1 Receptor Agonist with Unprecedented Selectivity and Procognitive Potential," Journal of Medicinal Chemistry, vol. 53, pp. 6386-6397 (2010), American Chemical Society.

E.S. Slavov et al., "Cytokine production in thromboangitis obliterans patients: New evidence for an immune-mediated inflammatory disorder," Clinical and Experimental Rheumatology, 23, pp. 219-226 (2005).

M. Sokolowska-Wojdyto et al., "Association of distinct IL-31 polymorphisms with pruritus and severity of atopic dermatitis," Journal of the European Academy of Dermatology and Venereology—Letters to the Editor, vol. 27, pp. 662-664 (2013).

T. Southworth et al., "IFN-γ synergistically enhances LPS signalling in alveolar macrophages from COPD patients and controls by corticosteroid-resistant STAT1 activation," British Journal of Pharmacology, vol. 166, pp. 2070-2083 (2012), The British Pharmacological Society.

B. Strober et al., "Effect of tofacitinib, a Janus kinase inhibitor, on haematological parameters during 12 weeks of psoriasis treatment," British Journal of Dermatology, vol. 169, pp. 992-999 (2013), British Association of Dermatologists.

Yoko Takanami-Ohnishi et al., "Essential Role of p38 Mitogen-activated Protein Kinase in Contact Hypersensitivity," The Journal of Biological Chemistry, vol. 277, No. 40, pp. 37896-37903 (2002), The American Society for Biochemistry and Molecular Biology, Inc.

Kenchi Takenaka et al., "Successful treatment of refractory aortitis in antineutrophil cytoplasmic antibody-associated vasculitis using tocilizumab," Clinical Rheumatology, vol. 33, pp. 287-289 (2014), Springer Nature.

A. Vaglio et al., "Eosinophilic granulomatosis with polyangiitis (Churg-Strauss): state of the art," Allergy, vol. 68, pp. 261-273 (2013), John Wiley & Sons A/S.

William Vainchenker et al., "JAKs in pathology: Role of Janus kinases in hematopoietic malignancies and immunodeficiencies," Seminars in Cell & Developmental Biology, vol. 19, pp. 385-393 (2008), Elsevier Ltd.

\* cited by examiner

CRYSTAL OF COMPOUND HAVING JAK-INHIBITING ACTIVITY

CROSS REFERENCE TO RELATED APPLICATIONS

This patent application is a continuation of co-pending U.S. application Ser. No. 16/077,889 filed on Aug. 14, 2018, which is a U.S. national stage application under 35 U.S.C. § 371 of International Patent Application No. PCT/JP2017/007594 filed on Feb. 28, 2017, which claims the benefit of foreign priority to Japanese Patent Application No. JP 2016-039315 filed on Mar. 1, 2016, the disclosures of all of which are hereby incorporated by reference in their entireties. The International Application was published in Japanese on Sep. 8, 2017, as International Publication No. WO 2017/150477 A1 under PCT Article 21(2).

FIELD OF THE INVENTION

The present invention relates to a novel compound with a JAK1 inhibitory activity.

BACKGROUND ART

Tyrosine kinases are a group of enzymes that specifically phosphorylate a tyrosine residue in proteins. The enzymes have a significant role in the intracellular signal transduction pathways and relate to a wide variety of biological functions including cell survival, differentiation, proliferation, and secretion. Janus Kinase (also referred to as JAK) family is known as that of intracellular tyrosine kinases involving a cytokine signaling. JAK family includes the four types of enzymes: JAK1, JAK2, JAK3 and Tyrosine Kinase 2 (also referred to as Tyk2). Once a cytokine associates with its respective cytokine receptor, JAK is phosphorylated, and a tyrosine residue of the receptor is then phosphorylated. Then, signal transducer and activator of transcription (also referred to as "STAT"), which exists in cells, will become associated with the phosphorylated tyrosine residue of the receptor, and a tyrosine residue of STAT is phosphorylated by JAK. The phosphorylated STATs form a dimer, and the dimer translocates into the nucleus and activates transcription of target gene, which leads to activation of the cells. JAK/STAT pathways are the key intracellular signal transduction pathways of cytokines in immunocompetent cells (Non-Patent Literature 1). About 40 types of cytokine signal transductions are mediated by a combination of the four JAKs and seven STATs, and abnormalities of a cytokine production and a cytokine signaling are believed to have an intimate involvement in not only various immune and inflammatory diseases, such as autoimmune diseases and allergic diseases, but also diseases having diverse pathologies such as cancers. Compounds suppressing the activation of these JAK/STAT pathways draw attention as new therapeutics for these diseases, and, in fact, JAK inhibitors have already been approved in the United States and Japan as a therapeutic for myelofibrosis, polycythemia vera and rheumatoid arthritis. Further, effects of such compounds are expected in the treatment of other autoimmune diseases (such as psoriatic arthritis, juvenile arthritis, Castleman's disease, systemic lupus erythematosus, Sjögren's syndrome, multiple sclerosis, inflammatory bowel disease, Behçet's disease, myasthenia gravis, type 1 diabetes mellitus, immunoglobulin nephropathy, autoimmune thyroid diseases, psoriasis, scleroderma, lupus nephritis, dry eye, vasculitis (such as Takayasu's arteritis, giant cell arteritis, microscopic polyangiitis, granulomatosis with polyangiitis and eosinophilic granulomatosis with polyangiitis), dermatomyositis, polymyositis and neuromyelitis optica), inflammatory diseases (such as atopic dermatitis, contact dermatitis, eczema, pruritus, food allergies, bronchial asthma, eosinophilic pneumonia, chronic obstructive pulmonary disease, allergic rhinitis, chronic sinusitis, eosinophilic sinusitis, nasal polyp, allergic conjunctivitis, osteoarthritis, ankylosing spondylitis, Kawasaki disease, Buerger's disease, polyarteritis nodosa and IgA vasculitis), proliferative diseases (such as solid cancers, blood cancers, lymph malignant tumor, myeloproliferative diseases, multiple myeloma, pulmonary fibrosis and eosinophilia), sudden hearing loss, diabetic nephropathy, alopecia areata, bone marrow transplant rejection or organ transplant rejection. Currently, the clinical trials are in progress for some diseases as listed above in Japan, the United States and Europe.

Specifically, various biological studies have demonstrated an important role of JAK1 in the signal transductions of many cytokines (See Non-Patent Literatures 2, 3 and 4), indicating that JAK1 inhibitors are useful in the treatment of the diseases, such as autoimmune diseases: psoriatic arthritis (See Non-Patent Literature 5), juvenile arthritis (See Non-Patent Literature 6), Castleman's disease (See Non-Patent Literature 6), systemic lupus erythematosus (See Non-Patent Literature 7), Sjögren's syndrome (See Non-Patent Literature 8), multiple sclerosis (See Non-Patent Literature 9), inflammatory bowel disease (See Non-Patent Literature 10), Behçet's disease (See Non-Patent Literature 11), myasthenia gravis (See Non-Patent Literature 12), type 1 diabetes mellitus (See Non-Patent Literature 9), immunoglobulin nephropathy (See Non-Patent Literature 13), autoimmune thyroid diseases (See Non-Patent Literature 14), psoriasis (See Non-Patent Literature 15), scleroderma (See Non-Patent Literature 16), lupus nephritis (See Non-Patent Literature 17), dry eye (See Non-Patent Literature 18), vasculitis (See Non-Patent Literatures 19, 20, 21, 22 and 23), dermatomyositis (See Non-Patent Literature 24), polymyositis (See Non-Patent Literature 24), neuromyelitis optica (See Non-Patent Literature 25), inflammatory diseases: atopic dermatitis (See Non-Patent Literature 26), contact dermatitis (See Non-Patent Literature 27), eczema (See Non-Patent Literature 28), pruritus (See Non-Patent Literature 29), food allergies (See Non-Patent Literature 30), bronchial asthma (See Non-Patent Literature 31), eosinophilic pneumonia (See Non-Patent Literature 32), chronic obstructive pulmonary disease (See Non-Patent Literature 33), allergic rhinitis (See Non-Patent Literature 31), chronic sinusitis (See Non-Patent Literature 34), eosinophilic sinusitis, nasal polyp (See Non-Patent Literature 35), allergic conjunctivitis (See Non-Patent Literature 36), osteoarthritis (See Non-Patent Literature 37), ankylosing spondylitis (See Non-Patent Literature 6), Kawasaki disease (See Non-Patent Literature 38), Buerger's disease (See Non-Patent Literature 39), polyarteritis nodosa (See Non-Patent Literature 40), IgA vasculitis (See Non-Patent Literature 41), proliferative diseases: solid cancers, blood cancers, lymph malignant tumor, myeloproliferative diseases, multiple myeloma (See Non-Patent Literatures 42, 43 and 44), sudden hearing loss (See Non-Patent Literature 45), diabetic nephropathy (See Non-Patent Literature 46), alopecia areata (See Non-Patent Literature 47), bone marrow transplant rejection or organ transplant rejection, etc. For example, the following clinical trials are in progress.

(1) Rheumatoid arthritis (https://clinicaltrials.gov/NCT01888874 and NCT02049138), (2) Crohn's disease (https://clinicaltrials.gov/NCT02365649), (3) non small cell lung cancer (https://clinicaltrials.gov/NCT02257619),
(4) pancreatic cancer (https://clinicaltrials.gov/NCT01858883),
(5) myelofibrosis (https://clinicaltrials.gov/NCT01633372) and
(6) psoriasis (https://clinicaltrials.gov/NCT02201524).

Further, among the cytokine signalings associated with JAK1, the inhibitors for the following cytokines have already been launched.
(1) IL-6 (also referred to as interleukin-6): therapeutic agents for rheumatoid arthritis, juvenile arthritis and Castleman's disease (See Non-Patent Literatures 48, 49 and 50).
(2) IL-2: therapeutic agent for acute rejection following renal transplantation (See Non-Patent Literature 51). In addition, the clinical trials on the following cytokine inhibitors are in progress.
(3) IL-4 and IL-13: therapeutic agent for bronchial asthma, atopic dermatitis, eosinophilic sinusitis, nasal polyp and eosinophilic esophagitis (See Non-Patent Literature 31).
(4) IL-13: therapeutic agent for pulmonary fibrosis (See https://clinicaltrials.gov/NCT02036580).
(5) IL-5: therapeutic agent for bronchial asthma, chronic obstructive pulmonary disease, eosinophilia, eosinophilic granulomatosis with polyangiitis, eosinophilic esophagitis, eosinophilic sinusitis/nasal polyp and atopic dermatitis (See Non-Patent Literature 31 and Non-Patent Literature 52)
(6) IFNα (also referred to as interferon-α): therapeutic agent for systemic lupus erythematosus (See Non-Patent Literature 7).
(7) IL-31: therapeutic agent for atopic dermatitis (https://clinicaltrials.gov/NCT01986933).
(8) TSLP (also referred to as thymic stromal lymphopoietin): therapeutic agents for bronchial asthma (https://clinicaltrials.gov/NCT02054130) and atopic dermatitis (https://clinicaltrials.gov/NCT00757042).

Thus, the inhibition of JAK1 signal is a preferred means for the prevention or treatment of the diseases caused by an abnormality of JAK1, such as autoimmune diseases, inflammatory diseases and proliferative diseases.

As a JAK1 inhibitor, [1,2,4]triazolo[1,5-a]pyridines (See Patent Literatures 1 and 2), tricyclic pyrazinones (See Patent Literature 3), pyrrolopyrimidines (See Patent Literatures 4 to 7), phthalazines (See Patent Literature 8), imidazopyrrolopyridines (See Patent Literature 9 and Non-Patent Literature 53), diamino-1,2,4-triazoles (See Non-Patent Literature 54), pyrazolo[1,5-a]pyridines (See Patent Literature 10), imidazo[1,2-a]pyridines (See Patent Literatures 11 and 12), benzimidazoles (See Patent Literature 13), 7-azaindoles (See Patent Literature 14) are reported. However, none of the documents as mentioned disclose pyrazolo[5,1-b][1,3]thiazole compounds.

PRIOR ART DOCUMENTS

Non-Patent Literatures

[Non-Patent Literature 1] O'Shea et al., Immunity, 2012, 36, 542-550.
[Non-Patent Literature 2] O'Sullivan et al., Mol. Immunol., 2007, 44, 2497-2506.
[Non-Patent Literature 3] Quintás-Cardama et al., Nat. Rev. Drug Discov., 2011, 10, 127-140.
[Non-Patent Literature 4] Haan et al., Chem. Biol., 2011, 18, 314-323.0
[Non-Patent Literature 5] Gan et al., BioDrugs, 2013, 27, 359-373.
[Non-Patent Literature 6] Mihara et al., Clin. Sci. (Lond.), 2012, 122, 143-159.
[Non-Patent Literature 7] Wallace et al., 71st Ann. Meet. Am. Coll. Rheumatol., 2007, Abs. 1315.
[Non-Patent Literature 8] Gliozzi et al., J. Autoimmun., 2013, 40, 122-133.
[Non-Patent Literature 9] Neurath et al., Cytokine Growth Factor Rev., 2011, 22, 83-89.
[Non-Patent Literature 10] Vuitton et al., Curr. Drug Targets, 2013, 14, 1385-1391.
[Non-Patent Literature 11] Akdeniz et al., Ann. Acad. Med. Singapore, 2004, 33, 596-599.
[Non-Patent Literature 12] Dalakas, Ann. N.Y. Acad. Sci., 2012, 1274, 1-8.
[Non-Patent Literature 13] Goto et al., Clin. Immunol., 2008, 126, 260-269.
[Non-Patent Literature 14] Nanba et al., Thyroid, 2009, 19, 495-501.
[Non-Patent Literature 15] Strober et al., Br. J. Dermatol., 2013, 169, 992-999.
[Non-Patent Literature 16] Christner et al., Curr. Opin. Rheumatol., 2004, 16, 746-752.
[Non-Patent Literature 17] Dong et al., Lupus, 2007, 16, 101-109.
[Non-Patent Literature 18] Lim et al., Cornea, 2015, 34, 248-252.
[Non-Patent Literature 19] Saadoun et al., Arthritis Rheumatol., 2015, 67, 1353-1360.
[Non-Patent Literature 20] Kieffer et al., Rev. Med. Interne., 2014, 35, 56-59.
[Non-Patent Literature 21] Takenaka et al., Clin. Rheumatol., 2014, 33, 287-289.
[Non-Patent Literature 22] Kobold et al., Clin. Exp. Rheumatol., 1999, 17, 433-440.
[Non-Patent Literature 23] Vaglio et al., Allergy, 2013, 68, 261-273.
[Non-Patent Literature 24] Gono et al., Rheumatology, 2014, 53, 2196-2203.
[Non-Patent Literature 25] Araki et al., Neurology, 2014, 82, 1302-1306.
[Non-Patent Literature 26] Bao et al., JAKSTAT, 2013, 2, e24137.
[Non-Patent Literature 27] Takanami-Ohnishi et al., J. Biol. Chem., 2002, 277, 37896-37903.
[Non-Patent Literature 28] Antoniu, Curr. Opin. Investig. Drugs, 2010, 11, 1286-1294.
[Non-Patent Literature 29] Sokolowska-Wojdylo et al., J. Eur. Acad. Dermatol. Venereol., 2013, 27, 662-664.
[Non-Patent Literature 30] Brown et al., Eur. Food Res. Technol., 2012, 235, 971-980.
[Non-Patent Literature 31] Legrand et al., J. Allergy Clin. Immunol. Pract., 2015, 3, 167-174.
[Non-Patent Literature 32] Kita et al., Am. J. Respir. Crit. Care Med., 1996, 153, 1437-1441.
[Non-Patent Literature 33] Southworth et al., Br. J. Pharmacol., 2012, 166, 2070-2083.
[Non-Patent Literature 34] Van Zele et al., Allergy, 2006, 61, 1280-1289.
[Non-Patent Literature 35] Nabavi et al., Allergol. Immunopathol. (Madr.), 2014, 42, 465-471.
[Non-Patent Literature 36] Sakai et al., Curr. Eye Res., 2013, 38, 825-834.
[Non-Patent Literature 37] Beekhuizen et al., Eur. Cell Mater., 2013, 26, 80-90.
[Non-Patent Literature 38] Abe, Nihon Rinsho, 2014, 72, 1548-1553.

[Non-Patent Literature 39] Slavov et al., Clin. Exp. Rheumatol., 2005, 23, 219-226.
[Non-Patent Literature 40] Kawakami et al., Acta. Derm. Venereol. 2012, 92, 322-323.
[Non-Patent Literature 41] Gülhan et al., Pediatr. Nephrol., 2015, 30, 1269-1277.
[Non-Patent Literature 42] Costa-Pereira et al., Am. J. Cancer Res., 2011, 1, 806-816.
[Non-Patent Literature 43] Vainchenker et al., Semin. Cell Dev. Biol., 2008, 19, 385-393.
[Non-Patent Literature 44] Li et al., Neoplasia, 2010, 12, 28-38.
[Non-Patent Literature 45] Masuda et al., Otol. Neurotol., 2012, 33, 1142-1150.
[Non-Patent Literature 46] Donate-Correa et al., J. Diabetes Res., 2015, 948417.
[Non-Patent Literature 47] Zhang et al., Arch. Dermatol. Res., 2015, 307, 319-331.
[Non-Patent Literature 48] Nishimoto et al., J. Rheumatol., 2003, 30, 1426-1435.
[Non-Patent Literature 49] Yokota et al., LANCET, 2008, 371, 998-1006.
[Non-Patent Literature 50] Nishimoto et al., Blood, 2000, 95, 56-61.
[Non-Patent Literature 51] Nashan et al., LANCET, 1997, 350, 1193-1198.
[Non-Patent Literature 52] Kouro et al., Int. Immunol., 2009, 21, 1303-1309.
[Non-Patent Literature 53] Kulagowski et al., Journal of Medicinal Chemistry, 2012, 55, 5901-5921.
[Non-Patent Literature 54] Malerich et al., Bioorg. Med. Chem. Lett., 2010, 20, 7454-7457.

Patent Literature

[Patent Literature 1] WO 2010/149769
[Patent Literature 2] WO 2010/010190
[Patent Literature 3] WO 2012/085176
[Patent Literature 4] WO 2009/114512
[Patent Literature 5] WO 2011/075334
[Patent Literature 6] WO 2012/022045
[Patent Literature 7] WO 2012/054364
[Patent Literature 8] WO 2012/037132
[Patent Literature 9] WO 2011/086053
[Patent Literature 10] WO 2011/101161
[Patent Literature 11] WO 2011/076419
[Patent Literature 12] JP 2011/136925
[Patent Literature 13] WO 2005/066156
[Patent Literature 14] WO 2007/084557

SUMMARY OF THE INVENTION

Problem to be Solved by the Invention

An object of the present invention is to provide a compound with an excellent JAK1 inhibitory activity.

Means for Solving the Problem

The present invention is based on the inventor's discovery that a compound shown in the following (hereinafter referred to as "the compound of the invention") has an excellent JAK1 inhibitory activity.

The present invention includes the following (I) to (III).
(I) A compound described in any one of the following (1) to (6):

(1) Methyl [1-({6-[(2S)-butan-2-ylamino]-2-(pyrazolo[5,1-b][1,3]thiazol-7-yl)pyrimidin-4-yl}carbonyl)piperidin-4-yl]carbamate tosylate monohydrate;
(2) Methyl [1-({6-[(2R)-butan-2-ylamino]-2-(pyrazolo[5,1-b][1,3]thiazol-7-yl)pyrimidin-4-yl}carbonyl)piperidin-4-yl]carbamate tosylate monohydrate;
(3) Methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate tosylate monohydrate;
(4) Ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate;
(5) N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide; and
(6) N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide.

(II) A crystal described in any one of the following (1) to (6):

(1) A crystal of methyl [1-({6-[(2S)-butan-2-ylamino]-2-(pyrazolo[5,1-b][1,3]thiazol-7-yl)pyrimidin-4-yl}carbonyl)piperidin-4-yl]carbamate tosylate monohydrate characterized by an X-ray powder diffraction pattern obtained using copper Kα radiation, which comprises diffraction peaks at diffraction angles (2θ) of 12.6°, 13.3°, 17.3°, 20.0°, 20.4°, 21.3° and 22.3°;

(2) A crystal of methyl [1-({6-[(2R)-butan-2-ylamino]-2-(pyrazolo[5,1-b][1,3]thiazol-7-yl)pyrimidin-4-yl}carbonyl)piperidin-4-yl]carbamate tosylate monohydrate characterized by an X-ray powder diffraction pattern obtained using copper Kα radiation, which comprises diffraction peaks at diffraction angles (2θ) of 12.6°, 13.3°, 17.3°, 20.0°, 20.4°, 21.3° and 22.3°;

(3) A crystal of methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate tosylate monohydrate characterized by an X-ray powder diffraction pattern obtained using copper Kα radiation, which comprises diffraction peaks at diffraction angles (2θ) of 12.6°, 13.3°, 17.2°, 20.6° and 21.8°;

(4) A crystal of ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate characterized by an X-ray powder diffraction pattern obtained using copper Kα radiation, which comprises diffraction peaks at diffraction angles (2θ) of 12.0°, 13.8°, 15.0°, 16.0°, 19.4°, 20.9° and 21.9°;

(5) A crystal of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide characterized by an X-ray powder diffraction pattern obtained using copper Kα radiation, which comprises diffraction peaks at diffraction angles (2θ) of 11.1°, 12.9°, 15.4°, 17.8°, 21.2° and 22.3°; and (6) A crystal of N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide characterized by an X-ray powder diffraction pattern obtained using copper Kα radiation, which comprises diffraction peaks at diffraction angles (2θ) of 10.6°, 13.0°, 14.6°, 17.4°, 17.7°, 21.3° and 21.7°.

(III) A pharmaceutical composition comprising a compound described in (I) or (II) as an active ingredient.

When specifying a diffraction angle (2θ) for a diffraction peak in the working examples or in the claims, it should be understood that a specified diffraction angle may have an error within the range of ±0.2°, preferably within the range of ±0.1°.

The crystal of the invention has high purity and is also easy to handle. Therefore, the crystal of the invention is useful as a manufacturing source for industrial production of a medicine, i.e., a JAK inhibitor.

Figure 1:
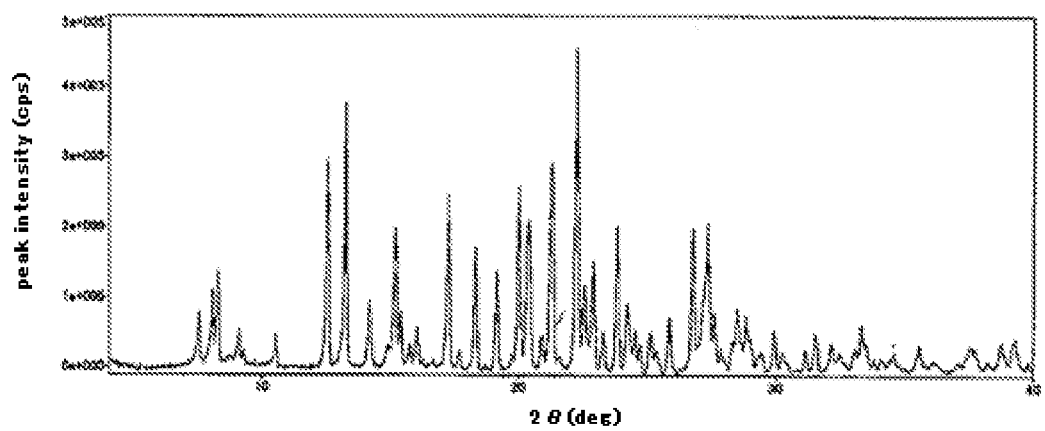
FIG. 1 is an X-ray powder diffraction pattern of the crystal of methyl [1-({6-[(2S)-butan-2-ylamino]-2-(pyrazolo[5,1-b][1,3]thiazol-7-yl)pyrimidin-4-yl}carbonyl)piperidin-4-yl]carbamate tosylate monohydrate, which comprises diffraction peaks at diffraction angles (2θ) of 12.6°, 13.3°, 15.2°, 17.3°, 18.3°, 19.1°, 20.0°, 20.4°, 21.3°, 22.3°, 23.8°, 26.8° and 27.4°. The vertical axis indicates the peak intensity (cps), and the horizontal axis indicates the diffraction angle (2θ[°]).

The terms as used herein are defined below.

The term "alkyl" includes, for example, an alkyl of straight or branched chain having 1 to 10 carbon atoms, preferably 1 to 8 carbon atoms, more preferably 1 to 6 carbon atoms. Specifically, the term may include, for example, methyl, ethyl, propyl, isopropyl, butyl, isobutyl, sec-butyl, tert-butyl, pentyl, sec-pentyl, 1-ethylpropyl, 1,2-dimethylpropyl, tert-pentyl, 2-methylbutyl, isopentyl, neopentyl, n-hexyl, sec-hexyl, 1-ethylbutyl, isohexyl, neohexyl, 1,1-dimethylbutyl, thexyl, 2-ethylbutyl, 1,2,2-trimethylpropyl, 2,2-dimethylbutyl, heptyl, isoheptyl, octyl and isooctyl.

The term "cycloalkyl" may include, for example, mono- to tri-cyclic saturated hydrocarbon group having 3 to 10 carbon atoms. Monocyclic cycloalkyl having 3 to 6 carbon atoms is preferable. Specifically, the term may include cyclopropyl, cyclobutyl, cyclopentyl, cyclohexyl, cycloheptyl, bicyclo[2.1.0]pentyl, bicyclo[2.2.1]heptyl, and bicyclo[2.2.2]octyl.

The term "aryl" refers to, for example, a mono- to tri-cyclic aromatic hydrocarbon group having 6 to 14 carbon atoms. Specifically, the term may include phenyl, 1-naphthyl, 2-naphthyl, 1-anthryl, 2-anthryl, 9-anthryl, 1-phenanthryl, 2-phenanthryl, 3-phenanthryl, 4-phenanthryl and 10-phenanthryl. Especially, phenyl is preferable.

MODE FOR CARRYING OUT THE INVENTION

The compound of the invention can be produced according to, for example, the following procedures and examples as described below, or methods known in the art, using a compound or an intermediate, which is available or can be prepared easily. In the case where a starting material has a functional group that may affect the reaction in the process for the production of the compound of the invention, the starting material should be protected with an appropriate protective group according to a known method in advance. The protective group can be removed by a known method after the reaction.

Scheme 1

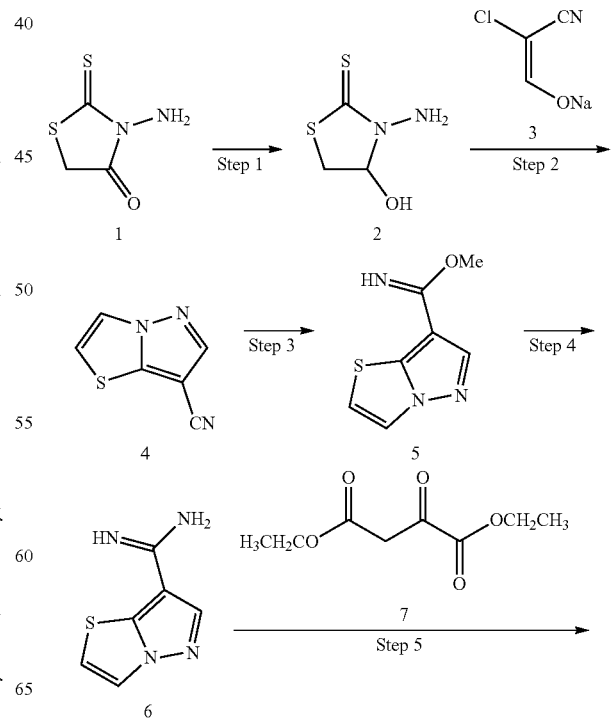

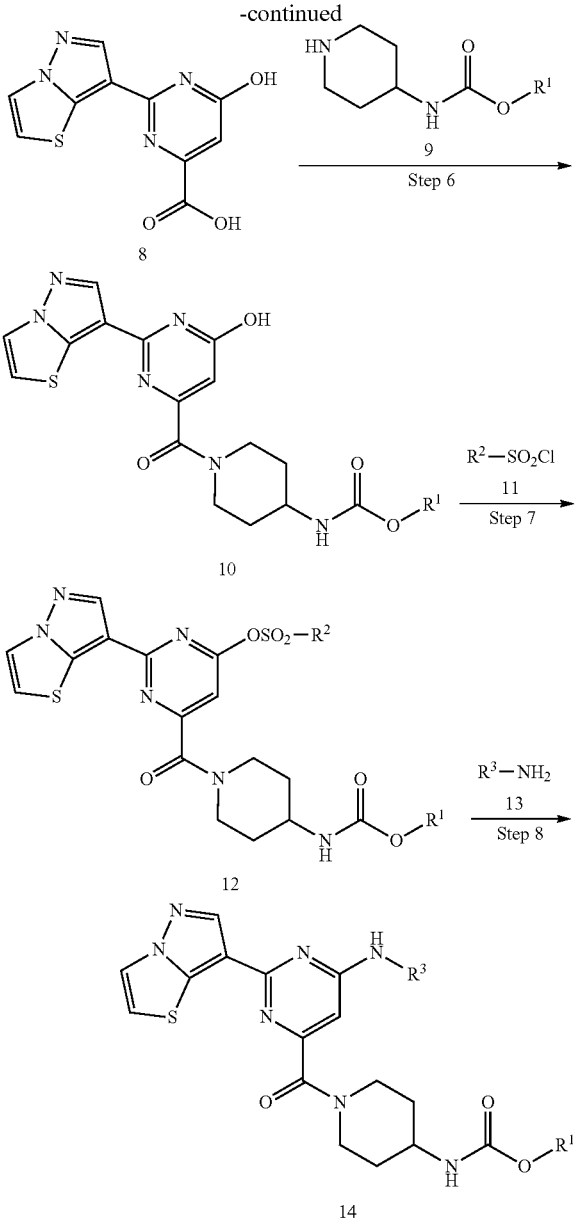

(wherein, $R^1$ is alkyl or cycloalkyl substituted by alkyl, $R^2$ is alkyl or aryl optionally substituted by alkyl, and $R^3$ is alkyl or cycloalkyl substituted by alkyl.)

Step 1

In this step, Compound 1 is reduced to obtain Compound 2.

Examples of the reducing agent to be used in this reaction include sodium borohydride, sodium triacetoxyborohydride and the like. Such reducing agent is preferably used in an amount within the range from 0.25 to 3 molar equivalents of Compound 1.

The solvent to be used in this reaction is not limited so long as it does not participate in the reaction, but examples thereof include ethers such as tetrahydrofuran (hereinafter referred to as "THF"), diethyl ether; alcohols such as methanol and ethanol; and a mixed solvent thereof.

The reaction temperature may be within the range from −78° C. to 100° C., preferably from −30° C. to 20° C.

The reaction time varies depending on the reaction temperature and the like, but it is generally within the range from 10 minutes to 24 hours.

Step 2

In this step, Compound 2 is dehydrated with an acid and then subjected to cyclization reaction with Compound 3 to obtain Compound 4.

Examples of the acid to be used in this reaction include sulfuric acid, methanesulfonic acid, p-toluenesulfonic acid, and the like. Such acid is preferably used in an amount within the range from 1 to 3 molar equivalents of Compound 2.

The solvent to be used in this reaction is not limited so long as it does not participate in the reaction, but examples thereof include alcohols such as 2-propanol and ethanol; nitriles such as acetonitrile and propionitrile; and a mixed solvent thereof.

The reaction temperature may be within the range from 0° C. to 100° C., preferably from 20° C. to 70° C.

The reaction time varies depending on the reaction temperature and the like, but it is generally within the range from 10 minutes to 2 hours for dehydration and is generally within the range from 30 minutes to 5 hours for cyclization.

Step 3

This step is conversion of nitrile compound 4 to the corresponding imidate compound 5 in the presence of a base, such as an alkali metal alkoxide, or an acid, such as hydrogen chloride, in a suitable solvent with stirring.

Examples of the base to be used in this reaction include alkoxides such as sodium methoxide and sodium ethoxide, and examples of the acid include gaseous hydrogen chloride. The hydrogen chloride may be prepared from acid chlorides, such as acetyl chloride, and alcohols, such as methanol and ethanol. Such base and acid are preferably used in an amount within the range from 1 to 100 molar equivalents of Compound 4.

The solvent to be used is not particularly limited so long as it does not participate in the reaction, but examples thereof include alcohols such as methanol, ethanol; ethers such as THF; and a mixed solvent thereof.

The reaction temperature may be within the range from −20° C. to 150° C., preferably from 0° C. to 100° C.

The reaction time varies depending on the reaction temperature and the like, but it is generally within the range from 30 minutes to 48 hours.

Step 4

This step is conversion of imidate compound 5 to the corresponding amidine compound 6 by reacting the imidate compound 5 with ammonia or an ammonium salt.

Examples of the ammonium salt to be used in this reaction include ammonium acetate, ammonium chloride and the like. Such ammonium salt or ammonia is preferably used in an amount within the range from 1 to 10 molar equivalents of the imidate compound 5.

If necessary, the reaction may be carried out in the presence of a base. Examples of such base to be used include organic bases such as triethylamine (hereinafter referred to as "TEA"), diisopropylethylamine (hereinafter referred to as "DIPEA") and the like.

The solvent to be used is not particularly limited so long as it does not participate in the reaction, but examples thereof include alcohols such as methanol, ethanol, and the like.

The reaction temperature may be within the range from −20° C. to 150° C., preferably from 0° C. to 100° C.

The reaction time varies depending on the reaction temperature and the like, but it is generally within the range from 30 minutes to 48 hours.

Step 5

In this step, amidine compound 6 is reacted with diethyl oxalacetate 7 or a salt thereof in the presence of a base in an appropriate solvent to obtain pyrimidine compound 8.

Examples of the base to be used include inorganic bases such as sodium hydroxide, potassium hydroxide, sodium carbonate and the like; alkoxides such as sodium methoxide, sodium ethoxide, and the like. The base is preferably used in an amount within the range from 1 to 50 molar equivalents of the amidine compound 6.

The solvent to be used in this reaction is not particularly limited so long as it does not participate in the reaction, but examples thereof include ethers such as THF, dimethoxyethane (hereinafter referred to as "DME"); alcohols such as methanol and ethanol; water; and a mixed solvent thereof.

The reaction temperature may be within the range from 0° C. to 200° C., preferably from 0° C. to 100° C.

The reaction time varies depending on the reaction temperature and the like, but it is generally within the range from 30 minutes to 24 hours.

Step 6

In this step, carboxylic acid 8 is coupled with amine compound 9 in an appropriate solvent to obtain Compound 10. Alternatively, an activated derivative of the carboxylic acid 8 may be reacted with Compound 9 to obtain Compound 10.

Examples of such activated derivative include acid halides such as acid chloride, mixed acid anhydrides, imidazolides, active amides, and the like, as conventionally used for amide condensation reaction.

In the case of using carboxylic acid 8, a condensing agent may be used, examples of which include 1,1'-carbonyldiimidazole (hereinafter referred to as "CDI"), 1-ethyl-3-(3-dimethylaminopropyl)carbodiimide (hereinafter referred to as "EDCI"), O-(7-azabenzotriazol-1-yl)-1,1,3,3-tetramethyluronium hexafluorophosphate (hereinafter referred to as "HATU"), diphenylphosphoryl azide, and the like. The amount of the condensing agent to be used in this reaction is suitably 1 to 3 molar equivalents of carboxylic acid 8.

If necessary, the reaction may be carried out in the presence of a base. Examples of such base to be used include organic bases such as TEA, DIPEA, pyridine and the like.

The solvent to be used in this reaction is not limited so long as it does not participate in the reaction, but examples thereof include ethers such as THF and DME; amides such as dimethylformamide (hereinafter referred to as "DMF"), N-methylpyrrolidone (hereinafter referred to as "NMP"), nitriles such as acetonitrile and propionitrile, and a mixed solvent thereof.

The reaction temperature may be within the range from −78° C. to 200° C., preferably from −20° C. to 50° C.

The reaction time varies depending on the reaction temperature and the like, but it is generally within the range from 10 minutes to 24 hours.

Step 7

In this step, Compound 10 is reacted with sulfonyl chloride 11 in an appropriate solvent to obtain Compound 12.

Examples of the sulfonyl chloride 11 to be used include methanesulfonyl chloride, p-toluenesulfonyl chloride, benzenesulfonyl chloride, and the like. The amount of the sulfonyl chloride 11 to be used is preferably 1 to 3 molar equivalents of Compound 10.

If necessary, the reaction may be carried out in the presence of a base. Examples of such base to be used include organic bases such as TEA, DIPEA, pyridine, and the like.

The solvent to be used in this reaction is not limited so long as it does not participate in the reaction, but examples thereof include ethers such as THF and DME; nitriles such as acetonitrile and propionitrile; amides such as DMF and NMP; and a mixed solvent thereof.

The reaction temperature may be within the range from −20° C. to 200° C., preferably from 0° C. to 100° C.

The reaction time varies depending on the reaction temperature and the like, but it is generally within the range from 30 minutes to 24 hours.

Step 8

In this step, Compound 12 is reacted with amine compound 13 in an appropriate solvent to obtain Compound 14.

The amount of the amine compound 13 to be used in this reaction is suitably 1 to 10 molar equivalents of Compound 12.

If necessary, the reaction may be carried out in the presence of a base. Examples of such base to be used include organic bases such as TEA, DIPEA, pyridine; inorganic bases such as sodium hydroxide, sodium bicarbonate, potassium carbonate, and the like.

The solvent to be used in this reaction is not limited so long as it does not participate in the reaction, but examples thereof include ethers such as THF and DME; nitriles such as acetonitrile and propionitrile; amides such as DMF and NMP; alcohols such as ethanol, isopropyl alcohol; and a mixed solvent thereof.

The reaction temperature may be within the range from 0° C. to 200° C., preferably from 20° C. to 150° C. The reaction may be carried out using microwave and/or under a sealed condition, if necessary.

The reaction time varies depending on the reaction temperature and the like, but it is generally within the range from 30 minutes to 24 hours.

A compound of the invention, which is a tosylate monohydrate, may be obtained by addition of p-toluenesulfonic acid monohydrate to a solution of free base of the compound.

The compound of the invention has JAK1 inhibitory activity as shown in the following test examples. Further, the compound of the invention also has anti-inflammatory, immunosuppressive and anti-proliferative effects etc., based on their JAK1 inhibitory activity.

Accordingly, the compound of the invention can be used as a preventive or therapeutic agent, for example, for the diseases associated with JAK1 and also the diseases for which the effect of the compound is expected in view of its anti-inflammatory, immunosuppressive and anti-proliferative effects etc.

Examples of specific diseases for which the compound of the invention can be applied include autoimmune disease (e.g., rheumatoid arthritis, psoriatic arthritis, juvenile arthritis, Castleman's disease, systemic lupus erythematosus, Sjögren's syndrome, multiple sclerosis, inflammatory bowel disease, Behçet's disease, myasthenia gravis, type 1 diabetes mellitus, immunoglobulin nephropathy, autoimmune thyroid diseases, psoriasis, scleroderma, lupus nephritis, dry eye, vasculitis (e.g., Takayasu's arteritis, giant cell arteritis, microscopic polyangiitis, granulomatosis with polyangiitis and eosinophilic granulomatosis with polyangiitis), dermatomyositis and polymyositis and neuromyelitis optica), inflammatory diseases (e.g., atopic dermatitis, contact dermatitis, eczema, pruritus, food allergies, bronchial asthma, eosinophilic pneumonia, chronic obstructive pulmonary disease, allergic rhinitis, chronic sinusitis, eosinophilic sinusitis, nasal polyp, allergic conjunctivitis, osteoarthritis, ankylosing spondylitis, Kawasaki disease, Buerger's disease, polyarteritis nodosa and IgA vasculitis), proliferative diseases (e.g., solid cancers, blood cancers, lymph malignant tumor, myeloproliferative diseases, multiple myeloma, pulmonary fibrosis and eosinophilia), sudden hearing loss, diabetic nephropathy, alopecia areata, bone marrow transplant rejection or organ transplant rejection.

The compound of the invention may be administered as a medicament to mammals, including human, as it is or as a pharmaceutical composition containing the same in an amount of, for example, 0.001% to 99.5%, preferably 0.1% to 90%, in combination with one or more pharmaceutically acceptable nontoxic and inactive carrier(s).

The carrier to be used may be one or more selected from solid, semi-solid, or liquid diluents, fillers, and other auxiliaries for pharmaceutical formulation. The pharmaceutical composition according to the invention may be administered in a unit dosage form. The pharmaceutical composition may be administered by interstitial, oral, intravenous, topical (e.g., transdermal, ocular instillation, intraperitoneal or intrathoracic administration) or transrectal administration. The composition should be administered in a dosage form suitable for these administration methods.

The dose of the compound should be adjusted taking into account the conditions of the patient, such as age, body weight, and the disease to be treated and the stage of the disease, the route of administration, and the compound to be administered, etc. In the case of oral administration to an adult, a typical daily dose of the compound of the invention or its pharmaceutically acceptable salt may be 0.01 mg to 5 g, and preferably 1 mg to 500 mg. In some cases, a lower dose may be sufficient, or conversely, a higher dose may be required. In general, the dose is given once a day or several times per day as divided portions, or in the case of intravenous administration, the medicine can be a bolus injection or continuously administered within 24 hours.

EXAMPLES

The invention is described in more detail with reference to the following Examples, Test Examples and Formulation Examples, which are not intended to limit the scope of the present invention.

The powder X-ray diffractometry was determined by using Rigaku Corporation's SmartLab (target: Cu, voltage: 45 kV, current: 200 mA, scan speed: 47.3 degrees/min).

Mass spectrometry was determined by using high performance liquid chromatography mass spectrometry. Electron spray ionization method was used as the ionization method. The measurements of the mass spectrometry are shown as m/z.

The measurement condition for high performance liquid chromatography mass spectrometry is as follows.
Analyzer: ACQUITY UPLC MS/PDA system (Waters)
Mass spectrometer: Waters 3100 MS detector
Photodiode array detector: ACQUITY PDA detector (UV Detection wavelength: 210 to 400 nm)
Column: Acquity BEH $C_{18}$, 1.7 μm, 2.1×50 mm
Flow rate: 0.5 mL/min
Column temperature: 40° C.
Solvent:
Solution A: 0.1% formic acid/$H_2O$ (v/v; the same hereinafter)
Solution B: 0.1% formic acid/acetonitrile The optical purity is determined by using high performance liquid chromatography (HPLC) under the following measurement condition.
Analyzer: SHIMADZU LC-10AS (SHIMADZU)
Detector: SPD-10A (SHIMADZU, UV Detection wavelength: 254 nm)
Column: Chiralcel AD-H, Φ4.6 mm×250 mm (Daicel)
Flow rate: 1 mL/min
Column temperature: 40° C.
Solvent: Hexane/Ethanol/Diethylamine=850/150/1 (v/v/v)

The abbreviations used in the Examples are as follows.
DMF: dimethylformamide
DMSO: dimethyl sulfoxide
DIPEA: N,N-diisopropylethylamine
TEA: triethylamine
THF: tetrahydrofuran
TFA: trifluoroacetic acid
NMP: N-methylpyrrolidone
HATU: O-(7-azabenzotriazol-1-yl)-1,1,3,3-tetramethyluronium hexafluorophosphate
MS: mass spectrometry
LCMS: high performance liquid chromatography mass spectrometry
ESI: electron spray ionization
M: molar concentration
v/v: volume/volume Reference Example 1: Pyrazolo[5,1-b][1,3]thiazole-7-carbonitrile Step 1: Preparation of 2-(thiazol-2-yl)acetonitrile Under ice cooling, 60% sodium hydride (7.9 g) was added portionwise to a solution of tert-butyl cyanoacetate (28 g) in DMF (100 mL), and the mixture was stirred for 10 minutes. To the mixture was added 2-bromothiazole (25 g), followed by stirring at room temperature for 15 minutes and then at 120° C. for 2 hours. To the mixture was added 1M aqueous hydrochloric acid, followed by extraction with ethyl acetate. The organic layer was washed with water, dried over anhydrous magnesium sulfate and concentrated under reduced pressure. The residue was washed with hexane, and then suspended in toluene (200 mL). To the suspension was added p-toluenesulfonic acid monohydrate (2.0 g), and the mixture was stirred at 105° C. for 2 hours. The mixture was diluted with ethyl acetate and washed with saturated aqueous sodium bicarbonate. The organic layer was dried over anhydrous magnesium sulfate and concentrated under reduced pressure. The residue was purified by silica gel column chromatography to yield the title compound (7.0 g).
MS (m/z): 125 $[M+H]^+$ Step 2: Preparation of pyrazolo[5,1-b][1,3]thiazole-7-carbonitrile Under ice cooling, to a solution of 2-(thiazol-2-yl)acetonitrile (5 g) obtained in Step 1 in dichloromethane (50 mL)

was added a solution of O-(mesitylsulfonyl)hydroxyamine (prepared as described in *Organic Process Research & Development*, 2009, 13, 263-267) in dichloromethane (20 mL). The mixture was stirred at room temperature for 2 hours, and diethyl ether was added to the mixture under ice cooling. The precipitated solid was collected by filtration, and the solid thus obtained was suspended in triethyl orthoformate (35 mL). The mixture was stirred at 120° C. for 1 hour and then concentrated under reduced pressure. The residue was purified by silica gel column chromatography to yield the title compound (2.5 g).

MS (m/z): 150 [M+H]$^+$

Reference Example 2: 6-Hydroxy-2-(pyrazolo[5,1-b][1,3]thiazol-7-yl)pyrimidine-4-carboxylic Acid To a solution of pyrazolo[5,1-b][1,3]thiazole-7-carbonitrile (6 g) obtained in Reference Example 1 in methanol (150 mL) was added 28% sodium methoxide in methanol (24.6 mL). The mixture was stirred at room temperature for 3 hours. Ammonium chloride (12.9 g) was added, and the mixture was stirred at 90° C. for 1 hour. The mixture was concentrated under reduced pressure. To the residue was added sodium diethyl oxaloacetate (33.8 g) in 5M aqueous sodium hydroxide (200 mL), and the mixture was stirred at 100° C. overnight. The mixture was acidified with conc. hydrochloric acid, and the precipitated solid was collected by filtration. The solid thus obtained was dissolved in 5M aqueous potassium hydroxide solution and washed with chloroform. The aqueous layer was acidified with conc. hydrochloric acid, and the precipitated solid was collected by filtration and dried to yield the title compound (10 g).

MS (m/z): 263 [M+H]$^+$

Reference Example 3: Methyl 6-chloro-2-(pyrazolo[5,1-b][1,3]thiazol-7-yl)pyrimidine-4-carboxylate 6-Hydroxy-2-(pyrazolo[5,1-b][1,3]thiazol-7-yl)pyrimidine-4-carboxylic acid (1.4 g) obtained in Reference Example 2 was suspended in phosphorus oxychloride (20 mL). Diethylaniline (1.6 g) was added, and the mixture was stirred at 130° C. for 2 hours. The reaction mixture was concentrated under reduced pressure, and methanol (100 mL) was added under ice cooling, and the mixture was stirred for 10 minutes. The mixture was diluted with chloroform and washed with water. The organic layer was dried over anhydrous magnesium sulfate and concentrated under reduced pressure. The residue was purified by silica gel column chromatography to yield the title compound (910 mg).

MS (m/z): 297 [M+H]$^+$

Reference Example 4: Methyl (1-{[6-chloro-2-(pyrazolo[5,1-b][1,3]thiazol-7-yl)pyrimidin-4-yl]carbonyl}piperidin-4-yl) carbamate 6-Hydroxy-2-(pyrazolo[5,1-b][1,3]thiazol-7-yl)pyrimidine-4-carboxylic acid (820 mg) obtained in Reference Example 2 was suspended in phosphorus oxychloride (5.0 mL). Diethylaniline (0.47 g) was added, and the mixture was stirred at 110° C. for 2 hours. The mixture was concentrated under reduced pressure and dissolved in dichloromethane (40 mL) under ice cooling. DIPEA (5.4 mL) and methyl piperidin-4-ylcarbamate (594 mg) were added, and the mixture was stirred at room temperature for 30 minutes. The mixture was diluted with chloroform and washed with saturated aqueous sodium bicarbonate. The organic layer was dried over anhydrous magnesium sulfate and concentrated under reduced pressure. The residue was purified by silica gel column chromatography to yield the title compound (910 mg).

MS (m/z): 421, 423 [M+H]$^+$

Reference Example 5: N-(1-{[6-chloro-2-(pyrazolo[5,1-b][1,3]thiazol-7-yl)pyrimidin-4-yl]carbonyl}piperidin-4-yl)cyclopropanecarboxamide The title compound was prepared as described in Reference Example 4 from 6-hydroxy-2-(pyrazolo[5,1-b][1,3]thiazol-7-yl)pyrimidine-4-carboxylic acid (8 g) obtained in Reference Example 2 using N-(piperidin-4-yl)cyclopropanecarboxamide (5.65 g, prepared as described in *Journal of Medicinal Chemistry*, 2010, 53, 6386-6397), instead of methyl piperidin-4-ylcarbamate, to yield the title compound (6.65 g).

MS (m/z): 431, 433 [M+H]$^+$

Reference Example 6: 6-{[(1S)-1-Cyclopropylethyl]amino}-2-(pyrazolo[5,1-b][1,3]thiazol-7-yl)pyrimidine-4-carboxylic Acid Step 1: Preparation of methyl 6-{[(1S)-1-cyclopropylethyl]amino}-2-(pyrazolo[5,1-b][1,3]thiazol-7-yl)pyrimidine-4-carboxylate To a solution of methyl 6-chloro-2-(pyrazolo[5,1-b][1,3]thiazol-7-yl)pyrimidine-4-carboxylate obtained in Reference Example 3 (1.0 g) in DMF (10 mL) were added DIPEA (1.8 mL) and (1S)-1-cyclopropylethanamine (320 mg), and the mixture was stirred at 80° C. for 3 hours. The mixture was purified by silica gel column chromatography to yield the title compound (1.1 g).

MS (m/z): 344 [M+H]$^+$

Step 2: Preparation of 6-{[(1S)-1-cyclopropylethyl]amino}-2-(pyrazolo[5,1-b][1,3]thiazol-7-yl)pyrimidine-4-carboxylic Acid To a solution of methyl 6-{[(1S)-1-cyclopropylethyl]amino}-2-(pyrazolo[5,1-b][1,3]thiazol-7-yl)pyrimidine-4-carboxylate obtained in Step 1 (600 mg) in THF (15 mL) and water (5 mL) was added lithium hydroxide monohydrate (100 mg), and the mixture was stirred at room temperature for 1 hour. The mixture was acidified with 1M hydrochloric acid, followed by distillation of THF off under reduced pressure, and extracted with chloroform. The organic layer was dried over anhydrous sodium sulfate and concentrated under reduced pressure to yield the title compound (470 mg).

MS (m/z): 330 [M+H]$^+$

Reference Example 7: 3-Amino-4-hydroxy-1,3-thiazolidine-2-thione

Sodium borohydride (19.1 g) was added to THF (750 mL), and slurry of N-aminorhodanine (250 g) in THF (500 mL) was added portionwise at below 5° C. After stirring for 30 minutes at below 5° C., methanol (111 mL) was added dropwise, and the mixture was stirred for 2 hours. Conc. hydrochloric acid (44 mL) was diluted with water (500 mL) and added dropwise to the mixture, and then water (1000 mL) was added dropwise, and the mixture was stirred for 1 hour at below 10° C. The precipitated crystals were filtered, washed with water (600 mL) and dried at 40° C. under reduced pressure to yield the title compound (209.1 g).
MS (m/z): 151 [M+H]+

Reference Example 8: Sodium 2-chloro-2-cyanoethen-1-olate

To a slurry of sodium methoxide (14.3 g) in cyclopentyl methyl ether (300 mL) were added dropwise methyl formate (17.5 g) at below 20° C. and then chloroacetonitrile (20 g), and the mixture was stirred for 3 hours at below 30° C. After completion of the reaction, precipitated crystals were filtered, washed with cyclopentyl methyl ether (40 mL), and dried at 40° C. under reduced pressure to yield the title compound (29.2 g).

Reference Example 9: Methyl pyrazolo[5,1-b][1,3]thiazole-7-carboximidate Hydrochloride To a slurry of 3-amino-4-hydroxy-1,3-thiazolidine-2-thione (50 g) in 2-propanol (250 mL) was added conc. sulfuric acid (48.97 g), and the mixture was stirred with heating at 80° C. for 1 hour. After cooling to below 40° C., acetonitrile (500 mL) and sodium 2-chloro-2-cyanoethen-1-olate (62.65 g) obtained in Reference Example 8 were added, and the mixture was stirred at 80° C. for 4 hours. After cooling, activated charcoal (10 g) was added, and the mixture was stirred at room temperature for 30 minutes. The mixture was filtered to remove insoluble materials and washed three times with acetonitrile (100 mL). The filtrate was concentrated under reduced pressure and then azeotroped three times with methanol (100 mL) to remove acetonitrile. Methanol (150 mL) and THF (150 mL) were added to the concentrate, which was then added to a solution of acetyl chloride (209 g) in methanol (350 mL) at below 20° C. After stirring overnight at room temperature, THF (350 mL) was added, and the mixture was stirred at below 10° C. for 1 hour. The precipitated crystals were filtered, washed with THF (300 mL) and dried at 50° C. under reduced pressure to yield the title compound (45.5 g).
MS (m/z): 182 [M+H]+

Reference Example 10: Pyrazolo[5,1-b][1,3]thiazole-7-carboximidamide Acetate Salt To a slurry of methyl pyrazolo[5,1-b][1,3]thiazole-7-carboximidate hydrochloride (200 g) in methanol (1000 mL) were added ammonium acetate (85.15 g) and then DIPEA (142.82 g), and the mixture was stirred at 65° C. for 1 hour. After completion of the reaction, the mixture was cooled and acetonitrile (2000 mL) was added dropwise at room temperature. After stirring for 1 hour at below 10° C., precipitated crystals were filtered, washed with acetonitrile (400 mL), and dried at 50° C. under reduced pressure to yield the title compound (185.12 g).
Elemental Analysis for $C_6H_6N_4S \cdot C_2H_4O_2$
Calcd. (%) C: 42.47, H: 4.46, N: 24.76. Found. (%) C: 42.18, H: 4.25, N: 24.41.

Reference Example 11: 6-Hydroxy-2-(pyrazolo[5,1-b][1,3]thiazol-7-yl)pyrimidine-4-carboxylic Acid To an aqueous solution (900 mL) of sodium hydroxide (39.08 g) was added sodium diethyl oxalacetate (130.65 g) at below 10° C., and the mixture was stirred for 1 hour. Pyrazolo[5,1-b][1,3]thiazole-7-carboximidamide acetate (90 g) was added to the mixture, and the mixture was stirred with heating at 50° C. for 3 hours. After cooling to below 30° C., the mixture was acidified to pH 1 to 2 with conc. hydrochloric acid (138 g), and then stirred overnight at room temperature. The precipitated crystals were collected by filtration, washed with water (360 mL), and dried at 60° C. to yield the title compound (107.17 g).
MS (m/z): 263 [M+H]+

Reference Example 12: Methyl {1-[6-hydroxy-2-(pyrazolo[5,1-b][1,3]thiazol-7-yl)pyrimidine-4-carbonyl]piperidin-4-yl}carbamate To a slurry of 6-hydroxy-2-(pyrazolo[5,1-b][1,3]thiazol-7-yl)pyrimidine-4-carboxylic acid (238 g) in DMF (714 mL) was added TEA (275.51 g), and the mixture was stirred at 50° C. for 30 minutes. After cooling to below 20° C., 1,1'-carbonyldiimidazole (323.76 g) was added. After stirring for 30 minutes, methyl piperidin-4-ylcarbamate tosylate (449.79 g) was added, and the mixture was stirred for 30 minutes. After completion of the reaction, acetonitrile (3570 mL) was added dropwise at room temperature, and the mixture was stirred overnight. The precipitated crystals were filtered, washed with acetonitrile (480 mL), and dried at 60° C. under reduced pressure to yield the title compound (377.79 g).
MS (m/z): 403 [M+H]+

Reference Example 13: 6-{4-[(Methoxycarbonyl)amino]piperidine-1-carbonyl}-2-(pyrazolo[5,1-b][1,3]thiazol-7-yl)pyrimidin-4-yl 4-methylbenzene-1-sulfonate To a slurry of methyl {1-[6-hydroxy-2-(pyrazolo[5,1-b][1,3]thiazol-7-yl)pyrimidine-4-carbonyl]piperidin-4-yl}carbamate (365 g) in acetonitrile (1825 mL) were added TEA (275.33 g) and then 4-toluenesulfonyl chloride (259.36 g), and the mixture was stirred with heating at 50° C. for 1 hour. After completion of the reaction, the mixture was cooled and water (3650 mL) was added dropwise at room temperature. After stirring the mixture for 1 hour at below 10° C., precipitated crystals were filtered, washed with water (730 mL), and dried at 60° C. under reduced pressure to yield the title compound (442.08 g).
MS (m/z): 557 [M+H]+

Example 1: Methyl [1-({6-[(2S)-butan-2-ylamino]-2-(pyrazolo [5,1-b][1,3]thiazol-7-yl)pyrimidin-4-yl}carbonyl)piperidin-4-yl]carbamate Tosylate Monohydrate Step 1: Preparation of methyl [1-({6-[(2S)-butan-2-ylamino]-2-(pyrazolo[5,1-b][1,3]thiazol-7-yl)pyrimidin-4-yl}carbonyl)piperidin-4-yl]carbamate To a solution of 6-{4-[(methoxycarbonyl)amino]piperidine-1-carbonyl}-2-(pyrazolo[5,1-b][1,3]thiazol-7-yl)pyrimidin-4-yl 4-methylbenzene-1-sulfonate obtained in Reference Example 13 (1.0 g) in acetonitrile (7.0 mL) were added DIPEA (0.67 g) and (2S)-butan-2-amine (0.4 g), and the mixture was sealed and heated with stirring at 100° C. for 2 hours. After completion of the reaction, the mixture was diluted with ethyl acetate and washed with water (30 mL) and brine (30 mL). The organic layer was dried over anhydrous magnesium sulfate, concentrated under reduced pressure, and purified by column chromatography to yield the title compound (650 mg). The optical purity of the title compound thus obtained was equal to or higher than 99%, as confirmed by high-performance liquid chromatography (retention time: 35.7 minutes).

MS (m/z): 458 [M+H]$^+$

Step 2: Preparation of methyl [1-({6-[(2S)-butan-2-ylamino]-2-(pyrazolo[5,1-b][1,3]thiazol-7-yl)pyrimidin-4-yl}carbonyl)piperidin-4-yl]carbamate Tosylate Monohydrate To methyl [1-({6-[(2S)-butan-2-ylamino]-2-(pyrazolo[5,1-b][1,3]thiazol-7-yl)pyrimidin-4-yl}carbonyl)piperidin-4-yl]carbamate obtained in Step 1 of Example 1 (202 mg) was added acetonitrile (5 mL), and the mixture was heated at 50° C. p-Toluenesulfonic acid monohydrate (83 mg) was added, and the mixture was stirred overnight at room temperature. The precipitated crystals were collected by filtration and dried under reduced pressure to obtain crystals of the title compound (210 mg). The X-ray powder diffraction spectrum is shown in FIG. 1. The elemental analysis showed that the crystal thus obtained is monohydrate.

Elemental Analysis for $C_2H_{27}N_7O_3S·C_7H_8O_3S·1.0H_2O$

Calcd. (%) C: 51.92, H: 5.76, N: 15.14. Found. (%) C: 51.54, H: 5.92, N: 15.03.

Example 2: Methyl [1-({6-[(2R)-butan-2-ylamino]-2-(pyrazolo[5,1-b][1,3]thiazol-7-yl)pyrimidin-4-yl}carbonyl)piperidin-4-yl]carbamate Tosylate Monohydrate Step 1: Preparation of methyl [1-({6-[(2R)-butan-2-ylamino]-2-(pyrazolo[5,1-b][1,3]thiazol-7-yl)pyrimidin-4-yl}carbonyl)piperidin-4-yl]carbamate To a solution of 6-{4-[(methoxycarbonyl)amino]piperidine-1-carbonyl}-2-(pyrazolo[5,1-b][1,3]thiazol-7-yl)pyrimidin-4-yl 4-methylbenzene-1-sulfonate obtained in Reference Example 13 (1.5 g) in acetonitrile (10 mL) were added DIPEA (1.0 g) and (2R)-butan-2-amine (0.59 g), and the mixture was sealed and heated with stirring at 100° C. for 2 hours. After completion of the reaction, the mixture was diluted with ethyl acetate and washed with water (50 mL) and brine (30 mL). The organic layer was dried over anhydrous magnesium sulfate, concentrated under reduced pressure, and purified by column chromatography to yield the title compound (0.93 g). The optical purity of the title compound thus obtained was equal to or higher than 99%, as confirmed by high-performance liquid chromatography (retention time: 29.1 minutes).

MS (m/z): 458 [M+H]$^+$

Figure 2:
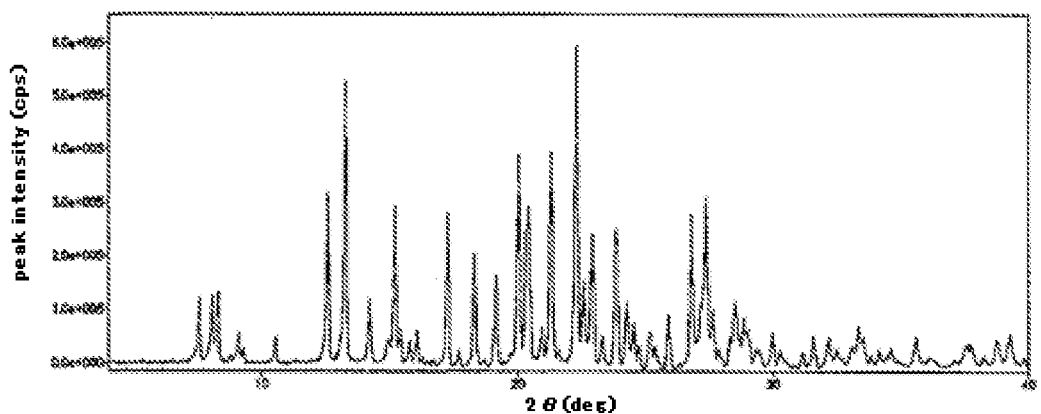
FIG. 2 is an X-ray powder diffraction pattern of the crystal of methyl [1-({6-[(2R)-butan-2-ylamino]-2-(pyrazolo[5,1-b][1,3]thiazol-7-yl)pyrimidin-4-yl}carbonyl)piperidin-4-yl]carbamate tosylate monohydrate, which comprises diffraction peaks at diffraction angles (2θ) of 12.6°, 13.3°, 15.2°, 17.3°, 18.3°, 19.2°, 20.0°, 20.4°, 21.3°, 22.3°, 23.8°, 26.8° and 27.4°. The vertical axis indicates the peak intensity (cps), and the horizontal axis indicates the diffraction angle (2θ[°]).

Step 2: Preparation of methyl [1-({6-[(2R)-butan-2-ylamino]-2-(pyrazolo[5,1-b][1,3]thiazol-7-yl)pyrimidin-4-yl}carbonyl)piperidin-4-yl]carbamate Tosylate Monohydrate To methyl [1-({6-[(2R)-butan-2-ylamino]-2-(pyrazolo[5,1-b][1,3]thiazol-7-yl)pyrimidin-4-yl}carbonyl)piperidin-4-yl]carbamate obtained in Step 1 of Example 2 (140 mg) was added acetonitrile (3.5 mL), and the mixture was heated at 50° C. p-Toluenesulfonic acid monohydrate (58 mg) was added, and the mixture was stirred overnight at room temperature. The precipitated crystals were collected by filtration and dried under reduced pressure to obtain crystals of the title compound (152 mg). The X-ray powder diffraction spectrum is shown in FIG. 2. The elemental analysis showed that the crystal thus obtained is monohydrate.

Elemental Analysis for $C_{21}H_{27}N_7O_3S·C_7H_8O_3S·1.0H_2O$

Calcd. (%) C: 51.92, H: 5.76, N: 15.14. Found. (%) C: 51.72, H: 5.84, N: 15.14.

Example 3: Methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Tosylate Monohydrate Step 1: Preparation of methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate To a solution of 6-{4-[(methoxycarbonyl)amino]piperidine-1-carbonyl}-2-(pyrazolo[5,1-b][1,3]thiazol-7-yl)pyrimidin-4-yl 4-methylbenzene-1-sulfonate obtained in Reference Example 13 (1.0 g) in acetonitrile (7.0 mL) were added DIPEA (0.69 g) and (1S)-1-cyclopropylethanamine (460 mg), and the mixture was sealed and heated with stirring at 100° C. for 2 hours. After completion of the reaction, the mixture was diluted with ethyl acetate and washed with water (50 mL) and brine (30 mL). The organic layer was dried over anhydrous magnesium sulfate, concentrated under reduced pressure, and purified by column chromatography to yield the title compound (720 mg).

Figure 3:
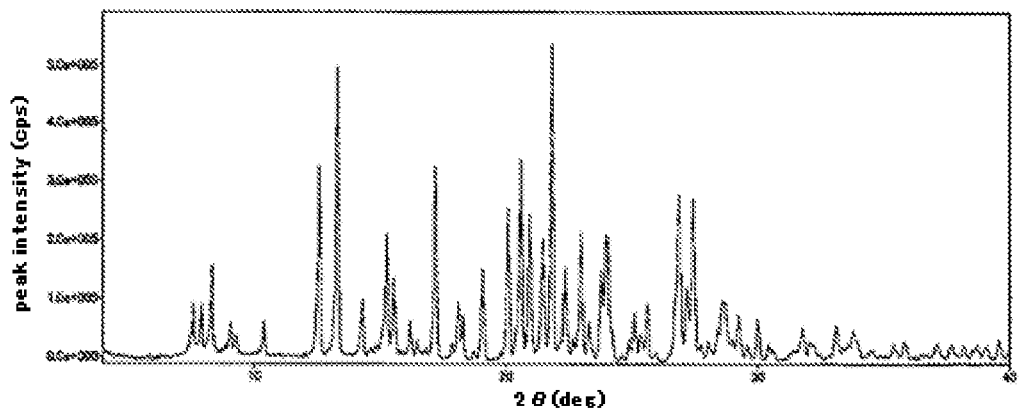
FIG. 3 is an X-ray powder diffraction pattern of the crystal of methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate tosylate monohydrate, which comprises diffraction peaks at diffraction angles (2θ) of 12.6°, 13.3°, 15.2°, 17.2°, 19.1°, 20.1°, 20.6°, 21.8°, 23.0°, 24.0°, 26.9° and 27.2°. The vertical axis indicates the peak intensity (cps), and the horizontal axis indicates the diffraction angle (2θ[°]).

Step 2: Preparation of methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate Tosylate Monohydrate To methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate obtained in Step 1 of Example 3 (201 mg) was added acetonitrile (5 mL), and the mixture was heated at 50° C. p-Toluenesulfonic acid monohydrate (81 mg) was added, and the mixture was stirred overnight at room temperature. The precipitated crystals were collected by filtration and dried under reduced pressure to obtain crystals of the title compound (237 mg). The X-ray powder diffraction spectrum is shown in FIG. 3. The elemental analysis showed that the crystal thus obtained is monohydrate.

Elemental Analysis for $C_{22}H_{27}N_7O_3S·C_7H_8O_3S·1.0H_2O$

Calcd. (%) C: 52.79, H: 5.65, N: 14.86. Found. (%) C: 52.72, H: 5.54, N: 14.82.

Specific optical rotation $[\alpha]_D^{25}=-44.4$ (c=1.00, DMSO)

Figure 4:
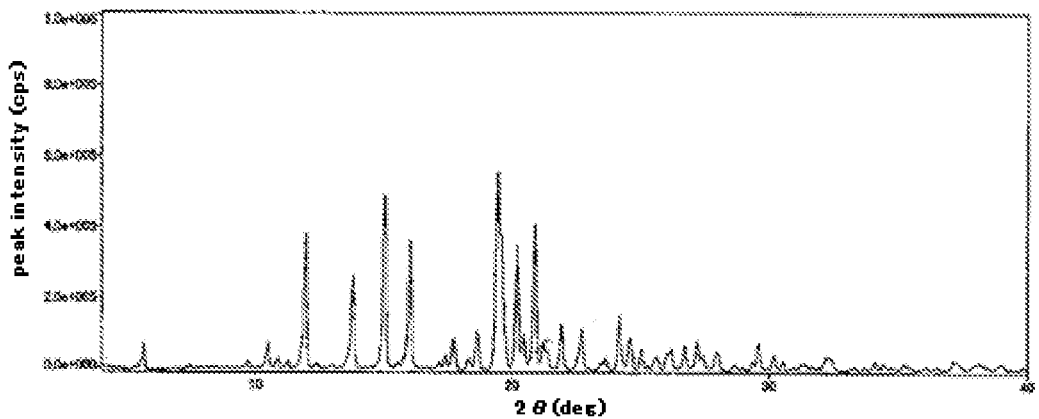
FIG. 4 is an X-ray powder diffraction pattern of the crystal of ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate, which comprises diffraction peaks at diffraction angles (2θ) of 12.0°, 13.8°, 15.0°, 16.0°, 17.7°, 18.6°, 19.4°, 19.6°, 20.2°, 20.9°, 21.9°, 22.7° and 24.1°. The vertical axis indicates the peak intensity (cps), and the horizontal axis indicates the diffraction angle (2θ[°]).

Example 4: Ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate To a solution of 6-{[(1S)-1-cyclopropylethyl]amino}-2-(pyrazolo[5,1-b][1,3]thiazol-7-yl)pyrimidin-4-carboxylic acid obtained in Reference Example 6 (640 mg) in DMF (5.0 mL) were added ethyl piperidin-4-ylcarbamate (310 mg, prepared as described in U.S. Pat. No. 4,918,073), DIPEA (730 μL) and HATU (1.1 g), and the mixture was stirred at room temperature for 1 hour. The mixture was purified by silica gel column chromatography to yield the title compound (410 mg). To the title compound (350 mg) was added ethyl acetate (7 mL), and the mixture was heated to dissolve the compound and stirred at room temperature for 20 hours. The precipitated crystals were collected by filtration and dried under reduced pressure to obtain crystals of the title compound (280 mg). The X-ray powder diffraction spectrum is shown in FIG. 4.

MS (m/z): 484 [M+H]$^+$
Elemental Analysis for $C_{23}H_{29}N_7O_3S$
Calcd. (%) C: 57.12, H: 6.04, N: 20.27.
Found. (%) C: 56.81, H: 6.12, N: 20.28.
Specific optical rotation $[\alpha]_D^{25}=-44.2$ (c=1.00, DMSO)

Figure 5:
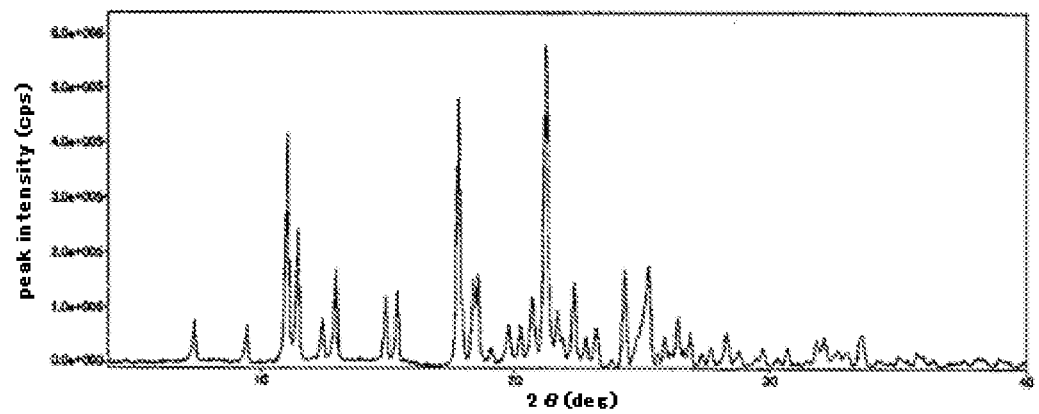
FIG. 5 is an X-ray powder diffraction pattern of the crystal of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide, which comprises diffraction peaks at diffraction angles (2θ) of 11.1°, 11.5°, 12.9°, 15.4°, 17.8°, 18.3°, 18.5°, 21.2°, 22.3°, 24.3°, and 25.2°. The vertical axis indicates the peak intensity (cps), and the horizontal axis indicates the diffraction angle (2θ[°]).

Example 5: N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide To a solution of 6-{[(1S)-1-cyclopropylethyl]amino}-2-(pyrazolo[5,1-b][1,3]thiazol-7-yl)pyrimidin-4-carboxylic acid obtained in Reference Example 6 (350 mg) in DMF (8.0 mL) were added N-(piperidin-4-yl)cyclopropanecarboxamide (268 mg), DIPEA (552 µL) and HATU (606 mg), and the mixture was stirred at room temperature for 1 hour. The mixture was purified by silica gel column chromatography to yield the title compound (410 mg). To the title compound (350 mg) was added ethyl acetate (7 mL), and the mixture was heated to dissolve the compound and stirred at room temperature for 20 hours. The precipitated crystals were collected by filtration and dried under reduced pressure to obtain crystals of the title compound (280 mg). The X-ray powder diffraction spectrum is shown in FIG. 5.

Elemental Analysis for $C_{24}H_{29}N_7O_2S$
Calcd. (%) C: 60.12, H: 6.09, N: 20.44.
Found. (%) C: 59.89, H: 6.37, N: 20.22.
MS (m/z): 480 [M+H]$^+$
Specific optical rotation $[\alpha]_D^{25}=-45.2$ (c=1.00, DMSO)

Figure 6:
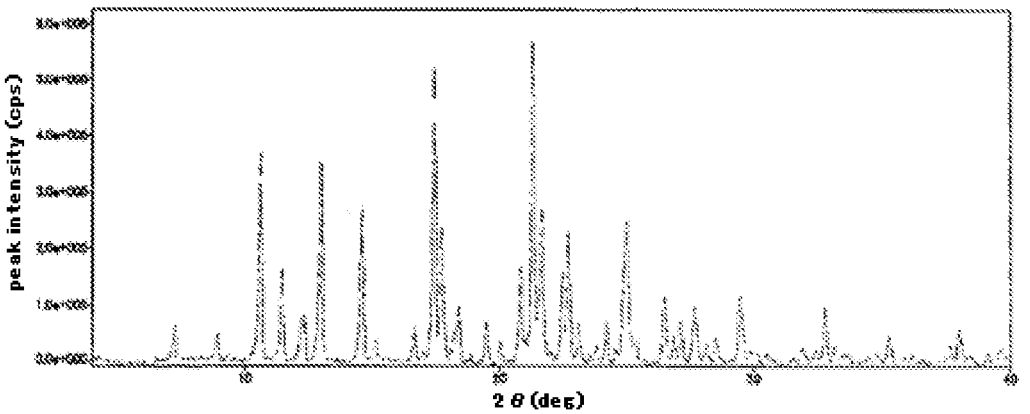
FIG. 6 is an X-ray powder diffraction pattern of the crystal of N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide, which comprises diffraction peaks at diffraction angles (2θ) of 10.6°, 13.0°, 14.6°, 17.4°, 17.7°, 20.8°, 21.3°, 21.7°, 22.7°, 25.0° and 26.5°. The vertical axis indicates the peak intensity (cps), and the horizontal axis indicates the diffraction angle (2θ[°]).

Example 6: N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide Under argon atmosphere, to a solution of N-(1-{[6-chloro-2-(pyrazolo[5,1-b][1,3]thiazol-7-yl)pyrimidin-4-yl]carbonyl}piperidin-4-yl)cyclopropanecarboxamide obtained in Reference Example 5 (550 mg) in tert-butanol (20 mL) were added TEA (534 µL) and (2R)-3,3-dimethylbutan-2-amine (258 mg), and the mixture was stirred at 90° C. overnight. The mixture was concentrated under reduced pressure. The residue was purified by silica gel column chromatography to yield the title compound (570 mg). To the title compound (100 mg) was added ethyl acetate (2 mL), and the mixture was heated to dissolve the compound and stirred at room temperature for 20 hours. The precipitated crystals were collected by filtration and dried under reduced pressure to obtain crystals of the title compound (70 mg). The X-ray powder diffraction spectrum is shown in FIG. 6.

Elemental Analysis for $C_{25}H_{33}N_7O_2S$
Calcd. (%) C: 60.58, H: 6.71, N: 19.78.
Found. (%) C: 60.2°, H: 6.96, N: 19.53.
MS (m/z): 496 [M+H]$^+$
Specific optical rotation $[\alpha]_D^{25}=+14.0$ (c=1.00, DMSO)

Test Example 1: Inhibitory Effect on JAK Tyrosine Kinase

1. Preparation of Test Compound

The test compound was dissolved in dimethyl sulfoxide (DMSO) to 10 mM and further diluted with DMSO to the concentrations of 1000, 100, 10, 1, 0.1 and 0.01 µM, respectively. For JAK1, these solutions of the test compound at the six concentrations 10 mM, 1000 µM, 100 µM, 10 µM, 1 µM and 0.1 µM were used. For JAK2 and JAK3, these solutions of the test compound at the six concentrations 1000 µM, 100 µM, 10 µM, 1 µM, 0.1 µM and 0.01 µM were used. The test compound solutions were diluted further to 20-fold with an assay buffer to obtain a sample solution. 15 mM Tris-HCl (pH7.5), 0.01 (v/v) % Tween-20 and 1 mM dithiothreitol were used as an assay buffer. DMSO was diluted to 20-fold with the assay buffer and was used as a negative control.

2. JAK Tyrosine Kinase Inhibitory Activity in the Presence of 1 mM ATP

The activity was determined by ELISA method. Each of the sample solutions was added to a streptavidin coated 96-well plate (DELFIA Strip Plate 8×12 well, PerkinElmer) at 10 µL/well (n=2). A substrate solution containing biotinylated peptide substrate (1250 nM for JAK1, 625 nM for JAK2 and JAK3), 2.5 mM ATP (final concentration 1 mM), 25 mM $MgCl_2$, 15 mM Tris-HCl (pH 7.5), 0.01 (v/v) % Tween-20 and 1 mM dithiothreitol, was added to the plate at 20 µL/well. Finally, JAK tyrosine kinase (Carna Biosciences, Inc.), which was previously diluted with the assay buffer to 7.5 nM for JAK1 and 0.75 nM for JAK2 and JAK3, was added to the plate at 20 µL/well, and the plate was incubated at 30° C. for 1 h. The plate was washed four times with buffer (50 mM Tris-HCl (pH 7.5), 150 mM NaCl, 0.02 (v/v) % Tween-20). A blocking buffer (0.1% Bovine Serum Albumin, 50 mM Tris-HCl (pH 7.5), 150 mM NaCl, 0.02 (v/v) % Tween-20) was added to the plate at 150 µL/well, and the plate was blocked at 30° C. for 1 h. The blocking buffer was removed, and a horse radish peroxidase-labeled anti-phosphorylated tyrosine antibody (BD Biosciences, Inc.) (diluted to 10000-fold with the blocking buffer) was added to the plate at 100 µL/well, and the plate was incubated at 30° C. for 30 min. The plate was washed with the washing buffer four times, and 3,3',5,5'-tetramethylbenzidine solution (Nacalai Tesque) was added to the plate at 100 µL/well to develop the color for 10 minutes. To the plate was added 0.1 M sulfuric acid at 100 µL/well to stop the reaction. The absorbance at 450 nm was measured using a microplate reader (BIO-RAD).

3. Analysis of the Results

A non-linear regression analysis using SAS system (SAS Institute Inc.) was performed for the absorbance as measured, and the concentration of the test compound that resulted in 50% inhibition of the respective tyrosine kinase activity ($IC_{50}$) was calculated. The results are shown in the following Table 1.

TABLE 1

| Test Compound (Example) | JAK1 Inhibitory Activity (IC50: nM) | JAK2 Inhibitory Activity (IC50: nM) | JAK3 Inhibitory Activity (IC50: nM) |
| --- | --- | --- | --- |
| 1 | 310 | 3700 | 3000 |
| 2 | 470 | 5700 | 6000 |
| 3 | 270 | 2600 | 1900 |
| 4 | 120 | 2100 | >10000 |
| 5 | 52 | 3400 | 3400 |
| 6 | 53 | 2200 | 2200 |

By using the compounds shown above in Test Example 1, the following tests (Test Examples 2, 3 and 4) are conducted.

Test Example 2: Inhibitory Effect on *Aspergillus*-Induced Airway Inflammation Model

*Aspergillus fumigatus* extracts (Greer laboratories, Inc.) are adjusted to 400 µg/mL with PBS. The *Aspergillus*

*fumigatus* solutions thus prepared are administered to mice as nasal drops (50 µL) on Day 0, Day 1, Day 7 and Day 8. The nasal drop is administered one hour after the administration of test compounds in the morning. The test compound is administered twice a day in the morning and evening of Day 0 to Day 9. The test compound is suspended in 0.5% methylcellulose at 10 mg/mL, and orally administered at the dosage of 10 mL/kg. The bronchoalveolar lavage fluid (BALF) is collected at Day 10, and the total white blood cell count in BALF is measured using Celltac (NIHON KOHDEN). The ratio of eosinophil in total white blood cell is calculated using ADVIA 120 (Siemens Healthcare Diagnostics), and the ratio is multiplied by the total white blood cell count to determine the eosinophil count in BALF. The inhibition rate of the test compound is determined, assuming the inhibitory ratio in the treatment with *Aspergillus fumigatus* extract and 0.5% methylcellulose as 0% and the inhibitory ratio in the treatment without *Aspergillus fumigatus* extract but with 0.5% methylcellulose as 100%.

Test Example 3: Inhibitory Effect on IL-4 Stimulated STAT6 Phosphorylation

1. Preparation of Test Compound

The test compound is dissolved in dimethyl sulfoxide (DMSO) to 10 mM, and further diluted with DMSO to the concentrations of 300 and 100 µM. The solution is further diluted with RPMI 1640 medium to 100-fold to obtain a sample solution. Also, DMSO is diluted to 100-fold with RPMI 1640 medium and is used as a negative control.

2. Phosphorylated STAT6 Activity

The sample solution or the negative control solution (50 µL) is mixed with a solution of DND39 cell (400 µL) (Cell number: $10^5$ cells) and shaken at 37° C. for 30 min. 50 µL of Interleukin-4 (10 ng/mL) is added as a stimulant, and the mixture is shaken for 15 min. 500 µL of Fixation buffer (BD Biosciences, Inc.) is added to the mixture, and the mixture is shaken for 10 min to stop the reaction. After centrifuge and removing the supernatant, 500 µL of a membrane permeabilizing agent Perm buffer III (BD Biosciences, Inc.) is added to the pellet, and is incubated at 4° C. for 30 min. After washing twice with a stain buffer (BD Biosciences, Inc.), Alexa Fluor 647 Mouse Anti-Stat6 (pY641) (BD Biosciences, Inc.) is added, and incubated in a cool dark place for 30 min. The obtained cell solution is subjected to a flow cytometer. The inhibition activity of the test compound is calculated, assuming the GEOMEAN value of the interleukin-4 stimulated negative control group fluorescence intensity as the inhibitory ratio of 0% and the GEOMEAN value of the non-stimulated negative control group fluorescence intensity as the inhibitory ratio of 100%. From the results, it is confirmed that the test compounds suppressed IL-4 signaling.

Test Example 4: Inhibitory Effect on IL-7 Stimulated STAT5 Phosphorylation

1. Preparation of Test Compound

The test compound is dissolved in dimethyl sulfoxide (DMSO) to 10 mM and further diluted with RPMI 1640 medium to 100-fold to prepare a sample solution. Also, DMSO is diluted with RPMI 1640 medium to 100-fold and is used as a negative control.

2. Phosphorylated STAT5 Activity

To 100 µL of human fresh blood is added 10 µL of the sample solution or the negative control solution, and shaken at 37° C. for 30 min. 10 µL of interleukin-7 (100 ng/mL) is added as a stimulant, and the mixture is shaken for 15 min. 1.4 mL of Lyse/fix buffer (BD Biosciences, Inc.), which is diluted to 5-fold by distilled water, is added to the reaction system. The mixture is shaken for 10 min, and centrifuged to separate cells. After removing the supernatant, 1 mL of PBS is added. After centrifuging to remove PBS, 500 µL of Perm buffer III (BD Biosciences, Inc.) is added, and is incubated at 4° C. for 30 min. After washing twice with Stain buffer (BD Biosciences, Inc.), Alexa Fluor 647 Mouse Anti-Stat5 antibody (pY694) (BD Biosciences, Inc.) is added, and incubated at cool dark place for 30 min. The obtained cell solution is subjected to a flow cytometer. The inhibition activity of the test compound is calculated, assuming the GEOMEAN value of the IL-7 stimulated negative control group fluorescence intensity as the inhibitory ratio of 0% and the GEOMEAN value of the non-stimulated negative control group fluorescence intensity as the inhibitory ratio of 100%. From the result, it is confirmed that the test compounds suppressed IL-7 signaling.

As shown in Test Examples 1 to 4, the compound of the invention showed JAK1 inhibitory activity, and thus, is effective against in vivo inflammation model.

INDUSTRIAL APPLICABILITY

In view of the fact that the compound of the invention exhibits JAK1 inhibitory activity, it is useful as a therapeutic agent for an autoimmune disease (e.g., rheumatoid arthritis, psoriatic arthritis, juvenile arthritis, Castleman's disease, systemic lupus erythematosus, Sjögren's syndrome, multiple sclerosis, inflammatory bowel disease, Behçet's disease, myasthenia gravis, type 1 diabetes mellitus, immunoglobulin nephropathy, autoimmune thyroid diseases, psoriasis, scleroderma, lupus nephritis, dry eye, vasculitis (e.g., Takayasu's arteritis, giant cell arteritis, microscopic polyangiitis, granulomatosis with polyangiitis and eosinophilic granulomatosis with polyangiitis), dermatomyositis, polymyositis and neuromyelitis optica), inflammatory diseases (e.g., atopic dermatitis, contact dermatitis, eczema, pruritus, food allergies, bronchial asthma, eosinophilic pneumonia, chronic obstructive pulmonary disease, allergic rhinitis, chronic sinusitis, eosinophilic sinusitis, nasal polyp, allergic conjunctivitis, osteoarthritis, ankylosing spondylitis, Kawasaki disease, Buerger's disease, polyarteritis nodosa and IgA vasculitis), proliferative diseases (e.g., solid cancers, blood cancers, lymph malignant tumor, myeloproliferative diseases, multiple myeloma, pulmonary fibrosis and eosinophilia), sudden hearing loss, diabetic nephropathy, alopecia areata, bone marrow transplant rejection or organ transplant rejection.

Formulation Example 1

Tablet (Oral Tablet)
In an 80 mg tablet of the formulation:

| | |
|---|---|
| Compound of Example 1 | 5.0 mg |
| Corn starch | 46.6 mg |
| Crystalline cellulose | 24.0 mg |
| Methylcellulose | 4.0 mg |
| Magnesium stearate | 0.4 mg |

According to a conventional method, a mixed powder of the components was tableted to form an oral tablet.

What is claimed is:
1. A method for treating atopic dermatitis, bronchial asthma, eosinophilic pneumonia, chronic obstructive pulmonary disease, eosinophilic sinusitis, nasal polyp, rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis, neuromyelitis optica, eosinophilia, or bone marrow transplant rejection, the method comprising the step of administering as an active ingredient a crystalline form of methyl [1-({6-[(2S)-butan-2-ylamino]-2-(pyrazolo[5,1-b][1,3]thiazol-7-yl)pyrimidin-4-yl}carbonyl)piperidin-4-yl]carbamate tosylate monohydrate characterized by an X-ray powder diffraction pattern obtained using copper Kα radiation, which comprises diffraction peaks at diffraction angles (2θ) of 12.6°, 13.3°, 17.3°, 20.0°, 20.4°, 21.3° and 22.3°.

2. A method for treating atopic dermatitis, bronchial asthma, eosinophilic pneumonia, chronic obstructive pulmonary disease, eosinophilic sinusitis, nasal polyp, rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis, neuromyelitis optica, eosinophilia, or bone marrow transplant rejection, the method comprising the step of administering as an active ingredient a crystalline form of methyl [1-({6-[(2R)-butan-2-ylamino]-2-(pyrazolo[5,1-b][1,3]thiazol-7-yl)pyrimidin-4-yl}carbonyl)piperidin-4-yl]carbamate tosylate monohydrate characterized by an X-ray powder diffraction pattern obtained using copper Kα radiation, which comprises diffraction peaks at diffraction angles (2θ) of 12.6°, 13.3°, 17.3°, 20.0°, 20.4°, 21.3° and 22.3°.

3. A method for treating atopic dermatitis, bronchial asthma, eosinophilic pneumonia, chronic obstructive pulmonary disease, eosinophilic sinusitis, nasal polyp, rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis, neuromyelitis optica, eosinophilia, or bone marrow transplant rejection, the method comprising the step of administering as an active ingredient a crystalline form of methyl (1-{6-{[(1S)-1-cyclopropylethyl]amino}-2-(pyrazolo[5,1-b][1,3]thiazol-7-yl)pyrimidin-4-yl]carbonyl}piperidin-4-yl)carbamate tosylate monohydrate characterized by an X-ray powder diffraction pattern obtained using copper Kα radiation, which comprises diffraction peaks at diffraction angles (2θ) of 12.6°, 13.3°, 17.2°, 20.6° and 21.8°.

4. A method for treating atopic dermatitis, bronchial asthma, eosinophilic pneumonia, chronic obstructive pulmonary disease, eosinophilic sinusitis, nasal polyp, rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis, neuromyelitis optica, eosinophilia, or bone marrow transplant rejection, the method comprising the step of administering as an active ingredient a crystalline form of ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate characterized by an X-ray powder diffraction pattern obtained using copper Kα radiation, which comprises diffraction peaks at diffraction angles (2θ) of 12.0°, 13.8°, 15.0°, 16.0°, 19.4°, 20.9° and 21.9°.

5. A method for treating atopic dermatitis, bronchial asthma, eosinophilic pneumonia, chronic obstructive pulmonary disease, eosinophilic sinusitis, nasal polyp, rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis, neuromyelitis optica, eosinophilia, or bone marrow transplant rejection, the method comprising the step of administering as an active ingredient a crystalline form of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide characterized by an X-ray powder diffraction pattern obtained using copper Kα radiation, which comprises diffraction peaks at diffraction angles (2θ) of 11.1°, 12.9°, 15.4°, 17.8°, 21.2° and 22.3°.

6. A method for treating atopic dermatitis, bronchial asthma, eosinophilic pneumonia, chronic obstructive pulmonary disease, eosinophilic sinusitis, nasal polyp, rheumatoid arthritis, juvenile arthritis, Castleman's disease, systemic lupus erythematosus, Sjögren's syndrome, inflammatory bowel disease, psoriasis, scleroderma, Takayasu's arteritis, giant cell arteritis, microscopic polyangiitis, granulomatosis with polyangiitis, eosinophilic granulomatosis with polyangiitis, neuromyelitis optica, eosinophilia, or bone marrow transplant rejection, the method comprising the step of administering as an active ingredient a crystalline form of N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide characterized by an X-ray powder diffraction pattern obtained using copper Kα radiation, which comprises diffraction peaks at diffraction angles (2θ) of 10.6°, 13.0°, 14.6°, 17.4°, 17.7°, 21.3° and 21.7°.

7. A method for producing a crystalline form of methyl [1-({6-[(2S)-butan-2-ylamino]-2-(pyrazolo[5,1-b][1,3]thiazol-7-yl)pyrimidin-4-yl}carbonyl)piperidin-4-yl]carbamate tosylate monohydrate characterized by an X-ray powder diffraction pattern obtained using copper Kα radiation, which comprises diffraction peaks at diffraction angles (2θ) of 12.6°, 13.3°, 17.3°, 20.0°, 20.4°, 21.3° and 22.3°, the method comprising the steps of:
reacting methyl [1-({6-[(2S)-butan-2-ylamino]-2-(pyrazolo[5,1-b][1,3]thiazol-7-yl)pyrimidin-4-yl}carbonyl)piperidin-4-yl]carbamate with p-toluenesulfonic acid monohydrate in acetonitrile while heating; and
subsequently crystallizing methyl [1-({6-[(2S)-butan-2-ylamino]-2-(pyrazolo[5,1-b][1,3]thiazol-7-yl)pyrimidin-4-yl}carbonyl)piperidin-4-yl]carbamate tosylate monohydrate by cooling the acetonitrile solution.

8. A method for producing a crystalline form of methyl [1-({6-[(2R)-butan-2-ylamino]-2-(pyrazolo[5,1-b][1,3]thiazol-7-yl)pyrimidin-4-yl}carbonyl)piperidin-4-yl]carbamate tosylate monohydrate characterized by an X-ray powder diffraction pattern obtained using copper Kα radiation, which comprises diffraction peaks at diffraction angles (2θ) of 12.6°, 13.3°, 17.3°, 20.0°, 20.4°, 21.3° and 22.3°, the method comprising the steps of:

reacting methyl [1-({6-[(2R)-butan-2-ylamino]-2-(pyrazolo[5,1-b][1,3]thiazol-7-yl)pyrimidin-4-yl}carbonyl)piperidin-4-yl]carbamate with p-toluenesulfonic acid monohydrate in acetonitrile while heating; and subsequently crystallizing methyl [1-({6-[(2R)-butan-2-ylamino]-2-(pyrazolo[5,1-b][1,3]thiazol-7-yl)pyrimidin-4-yl}carbonyl)piperidin-4-yl]carbamate tosylate monohydrate by cooling the acetonitrile solution.

9. A method for producing a crystalline form of methyl (14 [6-{[(1S)-1-cyclopropylethyl]amino-2-(pyrazolo[5,1-b][1,3]thiazol-7-yl)pyrimidin-4-yl]carbonyl}piperidin-4-yl) carbamate tosylate monohydrate characterized by an X-ray powder diffraction pattern obtained using copper Kα radiation, which comprises diffraction peaks at diffraction angles (2θ) of 12.6°, 13.3°, 17.2°, 20.6° and 21.8°, the method comprising the steps of:

reacting methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate with p-toluenesulfonic acid monohydrate in acetonitrile while heating; and subsequently crystallizing methyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate tosylate monohydrate by cooling the acetonitrile solution.

10. A method for producing a crystalline form of ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate characterized by an X-ray powder diffraction pattern obtained using copper Kα radiation, which comprises diffraction peaks at diffraction angles (2θ) of 12.0°, 13.8°, 15.0°, 16.0°, 19.4°, 20.9° and 21.9°, the method comprising the steps of:

dissolving ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate in ethyl acetate while heating; and subsequently crystallizing ethyl (1-{[6-{[(1S)-1-cyclopropylethyl]amino}-2-(pyrazolo[5,1-b][1,3]thiazol-7-yl)pyrimidin-4-yl]carbonyl}piperidin-4-yl)carbamate by cooling the ethyl acetate solution.

11. A method for producing a crystalline form of N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide characterized by an X-ray powder diffraction pattern obtained using copper Kα radiation, which comprises diffraction peaks at diffraction angles (2θ) of 11.1°, 12.9°, 15.4°, 17.8°, 21.2° and 22.3°, the method comprising the steps of:

dissolving N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide in ethyl acetate while heating; and subsequently crystallizing N-(1-{[6-{[(1S)-1-cyclopropylethyl]amino}-2-(pyrazolo[5,1-b][1,3]thiazol-7-yl)pyrimidin-4-yl]carbonyl}piperidin-4-yl)cyclopropanecarboxamide by cooling the ethyl acetate solution.

12. A method for producing a crystalline form of N-(1-{[6-{[(2R)-3,3-dimethylbutan-2-yl] amino}-2-(pyrazolo[5,1-1)] [1,3]thiazol-7-yl)pyrimidin-4-yl]carbonyl}piperidin-4-yl)cyclopropanecarboxamide characterized by an X-ray powder diffraction pattern obtained using copper Kα radiation, which comprises diffraction peaks at diffraction angles (2θ) of 10.6°, 13.0°, 14.6°, 17.4°, 17.7°, 21.3° and 21.7°, the method comprising the steps of:

dissolving N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide in ethyl acetate while heating; and subsequently crystallizing N-(1-{[6-{[(2R)-3,3-dimethylbutan-2-yl]amino}-2-(pyrazolo[5,1-b][1,3]thiazol-7-yl)pyrimidin-4-yl]carbonyl}piperidin-4-yl)cyclopropanecarboxamide by cooling the ethyl acetate solution.

* * * * *